(12) United States Patent
Fernández Martínez et al.

(10) Patent No.: US 10,130,461 B2
(45) Date of Patent: Nov. 20, 2018

(54) VARIABLE-POWER ACCOMMODATIVE INTRAOCULAR LENS AND ASSEMBLY OF VARIABLEPOWER ACCOMMODATIVE INTRAOCULAR LENS AND CAPSULAR RING

(71) Applicant: UNIVERSIDAD DE MURCIA, Murcia (ES)

(72) Inventors: Enrique Josua Fernández Martínez, Murcia (ES); Pablo Artal Soriano, Murcia (ES)

(73) Assignee: UNIVERSIDAD DE MURCIA, Murcia (ES)

( * ) Notice: Subject to any disclaimer, the term of this patent is extended or adjusted under 35 U.S.C. 154(b) by 63 days.

(21) Appl. No.: 14/439,619

(22) PCT Filed: Jul. 26, 2013

(86) PCT No.: PCT/ES2013/070551
§ 371 (c)(1),
(2) Date: Apr. 29, 2015

(87) PCT Pub. No.: WO2014/049185
PCT Pub. Date: Apr. 3, 2014

(65) Prior Publication Data
US 2015/0366660 A1 Dec. 24, 2015

(30) Foreign Application Priority Data
Sep. 28, 2012 (ES) .................................. 201231510

(51) Int. Cl.
*A61F 2/16* (2006.01)
(52) U.S. Cl.
CPC ........ *A61F 2/1635* (2013.01); *A61F 2/16015* (2015.04); *A61F 2/1624* (2013.01);
(Continued)

(58) Field of Classification Search
None
See application file for complete search history.

(56) References Cited

U.S. PATENT DOCUMENTS 3,305,294 A 2/1967 Alvarez
4,731,078 A * 3/1988 Stoy ...................... A61F 2/1648
623/6.13
(Continued)

FOREIGN PATENT DOCUMENTS

WO 2012/006186 A2 1/2012

OTHER PUBLICATIONS

Menapace, R., et al., "The capsular tension ring: Designs, applications, and techniques", J. Cataract Refract. Surg, vol. 26, Jun. 2000, pp. 898-912.
(Continued)

*Primary Examiner* — Leslie Lopez
(74) *Attorney, Agent, or Firm* — Ladas & Parry LLP

(57) ABSTRACT

The new variable power accommodative intraocular lens is comprised by a central body or optical zone that has at least four refracting interfaces that separate different materials. These are connected by means of a substrate that holds them in an equatorial manner, and which includes the bases of the fasteners of the lens embedded in its core. The lens changes its power in response to variations in the equatorial diameter of the materials that comprise the optical zone. Thanks to its design, the lens can achieve variations in the optical powers greater than one diopter per micrometer of equatorial compression. This is achieved through the real change of the curvature radii of the refracting interfaces that comprise the optical zone, as well as the central thicknesses along the length of the optical axis of the different materials that limit said refracting interfaces. Preferably the intraocular lens works in combination with a capsular ring, to which the haptics are fixed and whose external diameter determines the
(Continued)

power of the lens. The change of power mechanism in the lens initiates with the contraction of the ciliary muscle of the patient in response to the accommodative force.

14 Claims, 11 Drawing Sheets

(52) U.S. Cl.
CPC ...... *A61F 2/1694* (2013.01); *A61F 2002/169* (2015.04); *A61F 2002/1682* (2015.04); *A61F 2250/0053* (2013.01)

(56) References Cited

U.S. PATENT DOCUMENTS

| | | | |
|---|---|---|---|
| 5,112,351 A | 5/1992 | Christie et al. | |
| 5,158,572 A | 10/1992 | Nielsen | |
| 6,217,619 B1 | 4/2001 | Keller | |
| 6,635,306 B2 | 10/2003 | Steckl et al. | |
| 7,217,288 B2 | 5/2007 | Esch et al. | |
| 7,220,279 B2 | 5/2007 | Nun | |
| 7,260,734 B2 | 8/2007 | Labate et al. | |
| 7,421,009 B2 | 9/2008 | Kawamoto et al. | |
| 7,481,532 B2 | 1/2009 | Hong et al. | |
| 7,837,326 B2 | 11/2010 | Jethmalani et al. | |
| 7,871,437 B2 | 1/2011 | Hermans et al. | |
| 8,216,306 B2 | 7/2012 | Coroneo | |
| 2002/0107568 A1 | 8/2002 | Zadno-Azizi et al. | |
| 2003/0147046 A1* | 8/2003 | Shadduck | A61F 2/1613 351/159.69 |
| 2003/0187505 A1 | 10/2003 | Liao | |
| 2004/0015236 A1 | 1/2004 | Sarfarazi | |
| 2004/0249456 A1 | 12/2004 | Cumming | |
| 2005/0107875 A1 | 5/2005 | Cumming | |
| 2005/0125058 A1 | 6/2005 | Cumming et al. | |
| 2006/0271187 A1 | 11/2006 | Zadno-Azizi et al. | |
| 2007/0100444 A1 | 5/2007 | Brady et al. | |
| 2007/0100445 A1* | 5/2007 | Shadduck | A61F 2/1616 623/6.37 |
| 2007/0129801 A1 | 6/2007 | Cumming | |
| 2008/0027538 A1 | 1/2008 | Cumming | |
| 2008/0154363 A1 | 6/2008 | Cumming | |
| 2009/0030514 A1* | 1/2009 | Niwa | A61F 2/1613 623/6.54 |
| 2009/0234449 A1 | 9/2009 | De Juan, Jr. et al. | |
| 2009/0240328 A1 | 9/2009 | Treushnikov et al. | |
| 2009/0319040 A1 | 12/2009 | Khoury | |
| 2010/0094412 A1 | 4/2010 | Wensrich | |
| 2010/0097569 A1* | 4/2010 | Weeber | A61F 2/1618 351/159.44 |
| 2010/0100177 A1 | 4/2010 | Zhao | |
| 2010/0204788 A1 | 8/2010 | Van Noy | |
| 2010/0211171 A1 | 8/2010 | Sarfarazi | |
| 2010/0228346 A1 | 9/2010 | Esch | |
| 2010/0324672 A1 | 12/2010 | Esch et al. | |
| 2011/0035001 A1 | 2/2011 | Woods | |
| 2011/0071628 A1 | 3/2011 | Gross et al. | |
| 2011/0257742 A1 | 10/2011 | Bumbalough et al. | |
| 2012/0035724 A1 | 2/2012 | Clarke | |
| 2012/0168422 A1 | 7/2012 | Boyd et al. | |

OTHER PUBLICATIONS

International Search Report dated Jan. 23, 2014 for Application No. PCT/ES2013/070551.
D. J. Apple and J.D. Sims, "Harold Ridley and the invention of the intraocular lens", Survey of Opthalmology 40, 279-292, (1996).
S. A. Strenk, J. L. Semmlow, L. M. Strenk, P. Munoz, J. Gronlund-Jacob, J. K. DeMarco, "Age-related changes in human ciliary muscle and lens: a magnetic resonance imaging study," Invest. Ophthalmol. Vis. Sci. 40, 1162-69 (1999).
F. Manns, J. M. Parel, D. Denham, C. Billotte, N. Ziebarth, D. Borja, V. Fernandez, M. Aly, E. Arrieta, A. Ho, B. Holden,"Optomechanical response of human and monkey lenses in a lens stretcher," Invest. Ophthalmol. Vis. Sci. 48, 3260-3268 (2007).
S. Kasthurirangan, E. L. Markwell, D. A. Atchison, J. M. Pope, "MRI study of the changes in crystalline lens shape with accommodation and ageing in humans," Journal of Vision 11, 1-16 (2011).
S. Tamm, E. Tamm E, W. Rohen, "Age-related changes of the human ciliary muscle. A quantitative morphometric study," Mech. Ageing Dev. 62, 209-221 (1992).
N. M. Ziebarth, D. Borja, E. Arrieta, M. Aly, F. Manns, I. Dortonne, D. Nankivil, R. Jain, J. M. Parel, "Role of the lens capsule on the mechanical accommodative response in a lens stretcher," Invest. Ophthalmol. Vis. Sci. 49, 4490-4496 (2008).
A. Glasser, M. C. W. Campbell, "Presbyopia and optical changes in the human crystalline lens with age," Vision Research 38, 209-214 (1998).
A. Glasser, P. L. Kaufman, "Accommodation and presbyopia," in: P. L. Kaufman, A. Alm eds. Adler's Physiology of the Eye, Clinical Application. 10th ed. St Louis: Mosby; 197-233 (2003).
A. W. Lohmann, "A new class of varifocal lenses," Appl. Opt. 9 ,1669-1671 (1970).
O. Findl, C. Leydolt, "Meta-analysis of accommodating intraocular lenses," J. Cataract. Refract. Surg. 33, 522-527 (2007).
T. Nakamoto, "Origin of the capsular tension ring," J. Cataract Refract. Surg. 27, 1710-1711 (2001).
T. Hara, Y. Yamada, "Equator ring for maintenance of the completely circular contour of the capsular bag equator after cataract removal," Ophthalmic Surg. 22, 358-359 (1991).
H. V. Gimbel, R. Sun, "Clinical applications of capsular tension rings in cataract surgery," Ophthalmic Surg. Lasers 33, 44-53 (2002).
A. Márquez, C. Iemmi, J. Campos, J. Escalera, and M. Yzuel, "Programmable apodizer to compensate chromatic aberration effects using a liquid crystal spatial light modulator," Optics Express 13, 716-715 (2005).
Liou and Brennan, "Anatomically accurate, finite model eye for optical modeling," Journal of the Optical Society of America A 14, 1684-1695 (1997).
Gimbel, Howard V. Letter: "Role of Capsular Tension Rings in Preventing Capsule Contraction". J Cataract Refact Surg: vol. 26, p. 791-792, Jun. 2000.

* cited by examiner

VARIABLE-POWER ACCOMMODATIVE INTRAOCULAR LENS AND ASSEMBLY OF VARIABLEPOWER ACCOMMODATIVE INTRAOCULAR LENS AND CAPSULAR RING

RELATED APPLICATION INFORMATION

This application is a 371 of International Application PCT/ES2013/070551 filed 26 Jul. 2013, entitled "Variable-power Accommodative Intraocular Lens and Assembly of Variable-power Accommodative Intraocular Lens and Capsular Ring", which was published on 3 Apr. 2014, with International Publication Number WO2014/049185 A1, and claimed priority to Spain Patent Application No. P201231510 filed 28 Sep. 2012, the contents of which are incorporated herein by reference.

FIELD OF THE INVENTION

The present invention pertains to the group of accommodative intraocular corrective lenses for presbyopia. The invention refers to an intraocular lens that provides a variable optical power controlled by the contraction of the ciliary muscle, produced in response to the accommodative effort the subject, and a set comprising said lens and a capsular ring. The main use of the lens is to replace the natural crystalline lens, either because of the loss of transparency, or the loss of its capacity to vary its power. Therefore, the present invention pertains to the field of medical prostheses which are implanted in the eye.

PRIOR STATE OF THE ART

The Accommodation

The human eye has the capacity to adjust its optical power and thereby correctly focuses on objects or scenes located at different distances from the observer. This mechanism, which involves different aspects and physiological changes inside the eye, is called accommodation. The capacity to accommodate progressively weakens with age. This process of loss of accommodation is known as presbyopia. There are various factors that intervene in the development of presbyopia. It is known that the ciliary muscle essentially maintains its activity throughout the life of the subject. One part of the capacity of the ciliary muscle to contract is slightly affected during the ageing process. However, the small loss of strength in this muscle is not a factor that on its own causes presbyopia. In the same way, there are numerous ex vivo measures of the mechanical properties of the lens capsule which indicate that the changes in elasticity associated with ageing are likewise not responsible for presbyopia. Therefore, most of the changes associated with ageing that ultimately triggers the total loss of accommodation occur in the crystalline lens. This lens undergoes a notable change in its biomechanical properties, especially in regard to its Young' modulus, which makes it progressively stiffen as the subject ages. A significant change also occurs in the distribution of the index of refraction in the nucleus of the crystalline lens.

The knowledge of the different mechanisms that trigger presbyopia has opened the possibility of restoring accommodation in the eye with presbyopia by implanting a variable power intraocular lens. This must be done with an appropriate prosthesis which takes advantage of the mechanical forces that occur in the heart or the eye during the accommodative process for changing its power. As stated above, these forces and tensions essentially remain operative throughout the life of the subject.

This is precisely the essence of the invention described in this document. The novel design that is shown in the present invention makes it possible to take advantage of ciliary muscle contractions on the order of micrometers to produce changes in the optic power of the eye within the range of dioptres.

Intraocular Lenses

Nowadays, the surgical implantation of intraocular lenses as replacements of the natural crystalline lens is a routine intervention. The technique was introduced by Harold Ridley in 1949, based on observations of injuries that some military pilots suffered as a consequence of combat during the Second World War, as explained in detail in the work of D. J. Apple and J. D. Sims, "Harold Ridley and the invention of the intraocular lens", Survey of Opthalmology 40, 279-292, (1996).

Over the years the field of intraocular lenses has experienced an authentic revolution in every aspect. For instance, the materials employed in the lens has evolved from the practically rigid polymethylmethacrylate (PMMA), originally used by Ridley, to modern materials such as silicones and acrylics. These materials, thanks to their mechanical properties, can be folded prior to the implantation. This is done with corneal incisions on the order of 2-3 millimeters, thereby reducing complications associated with the surgery and making it minimally invasive.

There are even polymer materials with a shape and index of refraction that can be controlled from outside the eye with ultraviolet light irradiation. Regarding these materials there is, for example, document U.S. Pat. No. 7,421,009 B2, which provides details of their production and control. Essentially, the optical properties of these special materials can be manipulated within certain ranges with a controlled polymerization of them. The application of these photopolymerizable materials in intraocular lenses can be very advantageous, given that it enables ensuring an almost perfect emmetropia of the subject once implanted, while at the same time facilitating the generation of personalised refractive profiles. Along these lines, the applications centred in the field of ophthalmic optics, in particular for intraocular lenses, are detailed in the document U.S. Pat. No. 7,837,326 B2. One disadvantage of this technology compared to the implantation of traditional intraocular lenses, is the need for more post-operative follow up of the patient, specifically until the definitive polymerization of the material comprising the lens. Furthermore, during this lapse of time patients must also protect their eyes from ultraviolet radiation, which is responsible for polymerization, by wearing special glasses for this purpose. This technology does not have the capacity to change the optical power of the intraocular lens once the polymerization is blocked.

Normal intraocular lenses are designed to correct the far vision of the subject. They are called monofocal intraocular lenses. Thus, there is a large number of formulas that enable obtaining the necessary power for reaching the state of emmetropia in the patient with these monofocal lenses. These formulas are based on the previous measurement of certain biometric parameters of the eye, such as its axial length, the length of the anterior chamber, etc., as well as the estimate of the subjective refraction. At present, cataract operations have a high success rate, in most circumstances the calculations of the intraocular lens powers are accurate, and the large majority of patients obtain a final refraction for far vision of less than one dioptre. Therefore, people operated on for cataracts usually do not need glasses, or any other correction, for far vision.

However, cataract operations in which the natural crystalline lens is replaced with a prosthesis or intraocular lens go in tandem with the loss of the capacity to accommodate.

In this circumstance it is common that the large majority of people who are operated for cataracts are already presbyopic due to their age. This, however, is not a reason for considering that the loss of accommodation associated to the implantation of a monofocal lens is an inherent fact of the intervention. To the contrary, there are numerous examples, as have been pointed out above, that the rest of the elements involved in accommodation, such as the ciliary muscle, the lens capsule, and the zonular fibres, maintain their properties within reasonable limits until the end of life. Among the scientific articles that support the assertion made above are S. A. Strenk, J. L. Semmlow, L. M. Strenk, P. Munoz, J. Gronlund-Jacob, J. K. DeMarco, "Age-related changes in human ciliary muscle and lens: a magnetic resonance imaging study," Invest. Ophthalmol. Vis. Sci. 40, 1162-69 (1999); F. Manns, J. M. Parel, D. Denham, C. Billotte, N. Ziebarth, D. Borja, V. Fernandez, M. Aly, E. Arrieta, A. Ho, B. Holden, "Optomechanical response of human and monkey lenses in a lens stretcher," Invest. Ophthalmol. Vis. Sci. 48, 3260-3268 (2007); S. Kasthurirangan, E. L. Markwell, D. A. Atchison, J. M. Pope, "MRI study of the changes in crystalline lens shape with accommodation and ageing in humans," Journal of Vision 11, 1-16 (2011); S. Tamm, E. Tamm E, W. Rohen, "Age-related changes of the human ciliary muscle. A quantitative morphometric study," Mech. Ageing Dev. 62, 209-221 (1992); N. M. Ziebarth, D. Borja, E. Arrieta, M. Aly, F. Manns, I. Dortonne, D. Nankivil, R. Jain, J. M. Parel, "Role of the lens capsule on the mechanical accommodative response in a lens stretcher," Invest. Ophthalmol. Vis. Sci. 49, 4490-4496 (2008).

The loss of accommodation is basically explained by the changes the crystalline lens experiences with age. This has been demonstrated and corroborated by various studies, such as, for example: A. Glasser, M. C. W. Campbell, "Presbyopia and optical changes in the human crystalline lens with age," Vision Research 38, 209-214 (1998); A. Glasser, P. L. Kaufman, "Accommodation and presbyopia," in: P. L. Kaufman, A. Alm eds. Adler's Physiology of the Eye, Clinical Application. 10th ed. St Louis: Mosby; 197-233 (2003). Therefore, a prosthesis that has properties similar to those of the natural crystalline lens must be capable of returning the capacity of accommodative to the patient again.

This capacity for also seeing objects at short distances is not less, and definitively contributes to a person's quality of life and wellbeing. Not in vain has it been estimated that about 80% of the information and stimulus the human being receives on a day by day basis is obtained through the sense of sight. In our industrialised societies this percentage is possibly even higher, and is based mainly on near vision and middle distance vision.

Undoubtedly, one of the major limitations of conventional intraocular or monofocal lenses is their impossibility of changing their power once they are implanted in the eye. The vision of the subject on objects and scenes located at different distances would demand a simultaneous change in the power of the intraocular lens to maintain sharp the image projected on the retina. When the subject implanted with a fixed conventional intraocular lens fixes his vision on a nearby object, the image of it that their eye is capable of making on the retina is blurred. In this situation it becomes necessary to use glasses or other equivalent optical aids for near vision.

In the field of intraocular lens design, some partial solutions have been proposed to correct presbyopia and return the capacity of near and far sight to the subject without the need of additional optical aids. All of these solutions are encompassed in what is known as intraocular lens for presbyopia correction. To facilitate the explanation of its features and the current state of the art, a first division into two large categories may be made, based on the type of strategy that the lens design employs for providing correct near and far vision.

A first category can group together all those intraocular lenses for presbyopia correction that do not provide any change whatsoever with regard to their position within the eye after being implanted. In like manner, its shape and other parameters that define it from an optical and mechanical point of view do not change following the operation. This type of intraocular lenses is commonly called multifocal lenses. Its name is in specific reference to its operating principle. This is based on employing differentiated optical zones in the intraocular lens that create two or more focal points. These focal points produce a sharp image on the retina of planes located a different distances from the observer. There are numerous variations and designs. The large majority of them has radial symmetry around its optical axis. Thus, the different optical zones with different power are found on rings around the axis. One example in which the central zone is dedicated to near vision while the outer ring focuses distant objects is found in document U.S. Pat. No. 5,158,572 A. This design has the advantage of making use of the accommodative miosis to reduce the zone of far vision when nearby objects or scenes are observed. Accommodative miosis is a contraction of the pupil associated to the accommodative effort that the eye makes as a reflex when trying to see nearby objects. This arrangement of optical zones has, on the one hand, the problem of out of focus images when the patient tries to see far scenes under strong lighting conditions.

The optical zones of the intraocular lens can be given distinct powers through different strategies. The most extended alternative is to generate different focuses by employing focus zones with two or more continuous surfaces having different curvature radii, and also occasionally a different refraction index. The latter are called refractive intraocular lenses. The transition zones between zones may be more or less abrupt. For example, document 2010/0100177A1 discloses an intraocular lens with three refractive optical zones. One of the problems associated with this technology is the diffraction that produces the abrupt changes between optical zones with a different focus. This usually results in blurred vision due to halos. Some partial solutions to this problem have been proposed, such as using smooth aspheric surfaces for transition between zones, as shown in document US 005 112 351 A.

There are other possibilities for generating power. Thus, there are diffractive lenses whose principle is based on sampling light through a series of discrete zones with abrupt edges for producing a focus. An example of a diffractive lens is shown in document US 005 112 351 A. Another example with three differentiated zones for near, far, and intermediate vision is shown in US 007 481 532 B2.

There are also intraocular lenses with abrupt change zones based on what is called the Fresnel lens. An example of this type is shown in document US 2009/0240 328 A1.

At present, there are numerous designs of multifocal intraocular lenses that combine diffractive zones with refractive zones. A possible example of this technology is shown in document US 20 100 097 569 A1.

Multifocal lenses have some disadvantages and drawbacks for the patient, such as loss of sensitivity to contrast, appearance of halos, and an increase of optical aberrations, with the resulting detriment of the quality of the retinal image. In any case, these intraocular lenses only provide a partial solution to the vision at different distances. They only produce a sharp image of the planes for which have been designed, leaving the rest blurred. On the other hand, even when they are used for one of the distances for which they have been designed, another superimposed, blurred image appears, corresponding to the other focus. The blurring becomes even more evident as different foci are added. Even setting aside this effect, the zone of the intraocular lens that forms the correct image on the retina is significantly smaller than the pupil of the subject, and so the images have an attenuated intensity, which is one of the main causes of the loss of sensitivity to contrast.

The second category that can encompass intraocular lens for presbyopia correction covers pseudo-accommodative lenses. These have the main feature of taking advantage in a certain way the contraction of the ciliary muscle that is generated as a consequence of the accommodative effort. The ciliary muscle effort can generate diverse changes in the intraocular lens. Bearing in mind the nature of these changes, it is also possible to subdivide this genus of intraocular lenses into two species. On the one hand, there are the simple optical pseudo-accommodative lenses, in which the ciliary muscle provokes a change in the position of the lens with respect of the rest of the eye. This movement must be first and go towards the cornea, so as to increase the power of the entire eye. A second species within the pseudo-accommodative lenses includes compound optical intraocular lenses. These latter take advantage of the contraction of the ciliary muscle to change the relative distance between the elements or optical parts that shape the intraocular lens so as to be able to change the optical power of the set.

For the purpose of illustrating the current state of the art and its limitations, the following presents the most representative pseudo-accommodative lenses of each genus.

Document US 2011/0071 628 A1 shows a pseudo-accommodative lens shaped by separate optical elements. These actuate as independent lenses, and together produce the optical power needed to bring the eye to a state of emmetropia. The two lenses are connected by an external haptic, which is responsible for translating the change of tension of the zonule. The haptic is designed in such a way that the final net effect of compressing it translates into a change of the distance between the two lenses that comprise the set. The change of the distance between them produces an increase in the power of the lens, which is taken advantage of in order to focus on nearby objects.

Documents US2002/0107 568 A1 and US 2006/0271 187 A1, using a similar strategy, describe another fastener or haptic that also enables relative movement of the two lenses in order to change the optical power of the set. Its position for use is inside the lens capsule and its driving force is what generates the contraction of the ciliary muscle during accommodation. An alternative embodiment proposes the use of the periphery of one of the lenses for producing a different focus from the combination of both, which preferably is employed for near vision. This design would come with some of the drawbacks already described in the lenses for presbyopia correction, such as the appearance of halos in the vision, loss of sensitivity to contrast, etc.

Document US 2004/0015 236 A1, presents an intraocular lens with two different optical zones, which are joined together by fasteners or haptics designed to support the intraocular lens inside the lens capsule. The distance between these two elements defines the power of the set, as well as its capacity to increase it in response to an accommodative demand of the subject. Taking advantage of the same principle, document US2010/0211 171 A1 shows different variations of the haptics needed for implementing the double optic.

Taking advantage of the possibility of combining different materials, document US 2011/0035001 A1 shows a compound optical intraocular lens with two optical elements that change its relative distance in order to change the power of the set, as the operating principle.

There are compound optical designs that take advantage not only of the relative axial movements of the parts comprising the lens, but also rotational and even normal ones on the optical axis Taking advantage of the principle of the Alvarez lens described in U.S. Pat. No. 3,305,294 and in A. W. Lohmann, "A new class of varifocal lenses," Appl. Opt. 9, 1669-1671 (1970), document U.S. Pat. No. 7,871, 437 B2 describes a practical implementation that incorporates this technology inside an intraocular lens for presbyopia correction, by using some haptics specifically designed for this purpose.

Sometimes the design of the intraocular lens tries to make the lens capsule itself capable of changing the distance between the optical elements comprising it, but not transmitting the equatorial force, rather the force that is produced on its anterior and posterior faces. One example of this type of strategy, with two separated optical zones whose distance changes in order to produce the power increase, is found in document U.S. Pat. No. 6,217,619 B1. The haptic or haptic design does not allow implanting it through a small corneal incision, and so the surgery is significantly more invasive than is practised for foldable monofocal lenses. On the other hand, the lens capsule tends to wrap the haptic and with time generates new fibres, neutralising its possible capacity for changing its shape.

The following shows some examples of inventions related to intraocular lens for simple optical presbyopia correction.

Document US 2003/0187 505 A1 describes an intraocular lens consisting in an optical zone, and some peripheral haptics that enable its movement inside the lens capsule. This movement is produced by the contraction of the ciliary muscle. The haptics of the lens consist in a combination of stiff and flexible parts with the end purpose of producing an anterior movement of the entire lens in response to an external compression force. The document presents different possible variations for the design of the haptics.

Document US 2004/0249 456 A1 shows a flexible biconvex lens with some haptics, numbering two or more, which are capable of transmitting a contractile effort initiated by the ciliary muscle during an anterior shift of the lens. The haptics have frame types that allow movement of the lens in one single direction.

Along this same line are documents US 2005/0125058 A1 and US 2005/0107875 A1, which show some more elaborated haptics for this type of technology, all of them employing the hinge principle. Document US 2008/0154 363 A1 shows a design that employs the same principle with a system of double hinges, which in principle enables bigger shifts of the optics. Regarding the use of hinges in intraocular lenses, document U.S. Pat. No. 6,638,306 B2 provides a detailed description of the different possibilities that can be incorporated.

There are some studies that cast doubt on the capacity of this technology to provide changes of power beyond the depth of the focus due to the accommodative miosis. For example, the work of O. Findl, C. Leydolt, "Meta-analysis of accommodating intraocular lenses," J. Cataract. Refract. Surg. 33, 522-527 (2007) shows the lack of proof from a rigorous and statistical perspective, in regards to the improvement of near vision in patients implanted with three simple optical pseudo-accommodative lenses of three different companies.

Probably due to the lack of certainty regarding the operating principle of this technology, some improvement have been incorporated into the simple optical lenses, giving them features that are similar to multifocal lens. Along this line, Document US 2007/0129 801 A1 describes an intraocular lens design based on the aforementioned Document 2005/0107 875 A1, which also incorporates different optical zones with different power in order focus correctly at various distances. Another alternative design based on the same principle is described in Document US 2008/0027 538 A1, likewise presenting different optical zones with different powers.

The amount of power that can be added to the set comprising the eye and the intraocular lens when the latter moves inside the lens capsule is modest, around one dioptre. This means that the accommodation that is obtained with this type of strategy does not recover more than the natural pseudo-accommodative capacity of the subject, mainly due to the depth of the field. This is already obtained simply by the pupil contracting, done in tandem with the accommodation. Furthermore, the amount of variation due to shifting depends on the power of the implanted intraocular lens, which is a variable dependent on the biometric parameters of each patient. Therefore, in principle the generic capacity for varying the power of this type of lenses cannot be anticipated, given that it depends on the patient.

Within the classification of simple optical pseudo-accommodative lenses, there are designs that try to take advantage of the tension changes in the zonule as a consequence of the contraction of the ciliary muscle in order to change the shape of an optical zone or surface in combination with a shift. Attempts have also been made to take advantage of the vitreous body. In this case, the haptics are designed with a large contact surface towards the equatorial portion of the lens capsule so as to maximise the effect of the change of tension of the zonule. This goes in tandem with the drawback of requiring large corneal incisions to implant it in the eye. An example of this alternative is shown in document US 2009/0234 449 A1.

In the same direction of the document cited immediately above, there are some more sophisticated solutions that employ the power of the lens capsule to compress an internal system of chambers that transfer fluids from one to another, thus varying the power of the whole set. A document that discloses a technique as described is US 2010/0228 346 A. The complexity, stiffness and size of these types of solutions renders their viability difficult in a clinical setting. From a more basic point of view, the system of chambers blocks part of the incident light, creating diffraction figures which have a negative impact on vision quality.

There are designs taking advantage of this strategy by insufflating the fluid from the haptics in contact with the equatorial portion of the lens capsule up to the optical zone in order to vary the power of the intraocular lens during the accommodation. This assumes that the equatorial zone of the lens capsule increases its tension in a sufficient amount in order to deform the haptics and propel the fluid towards other chambers. Document U.S. Pat. No. 7,217,288 B2 provides an example of an intraocular lens that shows these features. The chamber system needed for this practical implementation forces the use of large corneal incisions for its implantation, due to the stiffness of the design.

Another intraocular lens that uses this same description is described in Document U.S. Pat. No. 7,260,737 B2. This design employs a sort of hydraulic jack that is capable of deforming the anterior surface of the intraocular lens when a fluid is insufflated into it from the equatorial haptics, which remain in contact with the lens capsule up to the central portion of the intraocular lens.

There is also another family of intraocular lenses that are placed in the posterior chamber, outside of the lens capsule and immediately behind the iris or pupil. It design, particularly in regard to the haptics, is significantly different from other intraocular lenses that are placed inside the lens capsule. In this modality, some partial solutions also appear to the problem of the power change in response to a demand of near vision. Among others, there is the design presented in Document U.S. Pat. No. 7,220,279 B2, in which the deformation induced by the pressure of the empty lens capsule on the lens is capable of deforming one of its surfaces, thereby increasing the power of the set.

In the document of T. Nakamoto, "Origin of the capsular tension ring," J. Cataract Refract. Surg. 27, 1710-1711 (2001) shows, for example, some details about capsular rings. These rings are routinely implanted during cataract operations through small corneal incisions. The technique is well established, regarding which there are numerous studies, for example, R. Menapace, O. Findl, M. Georgopoulos, "The capsular tension ring: designs, applications, and techniques," J. Cataract Refract. Surg. 26, 898-912 (2000). The intracapsular rings are especially recommended when there is a weakness in the zonule or in some part of the lens capsule, and they enable maintaining a circular equatorial profile of it, just as explained in the documents of T. Hara, Y. Yamada, "Equator ring for maintenance of the completely circular contour of the capsular bag equator after cataract removal," Ophthalmic Surg. 22, 358-359 (1991); H. V. Gimbel, R. Sun, "Role of capsular tension rings in preventing capsule contraction," J. Cataract Refract. Surg. 26, 791-792 (2000); H. V. Gimbel, R. Sun, "Clinical applications of capsular tension rings in cataract surgery," Ophthalmic Surg. Lasers 33, 44-53 (2002).

By analysing the most representative inventions of the current state of the art, it may be concluded that there are no intraocular lens design for presbyopia correction that works satisfactorily. For this, the intraocular lenses should simultaneously have a capacity for producing significant power changes of up to 4 refracting interfaces; simplicity regarding their design to make them commercially viable from the economic and technical point of view for their mass production; a similar optical quality of the retinal image for any distance of vision; and finally, although of paramount importance, the capacity to be implanted with minimal corneal incisions, or at least as small as the current state of the art, which can be set in a range of 2-3 millimeters.

SUMMARY OF THE INVENTION

Therefore, the subject matter of the present invention is to provide a variable power accommodative intraocular lens that gives a satisfactory response to each and every one of the aforesaid points.

For this, the subject intraocular lens of this invention can work directly in contact with the lens capsule (FIG. 3), or preferably in conjunction with a sort of capsular tension ring (FIG. 22), which has certain special features that will be described in this document.

The main use of the variable power intraocular lens described in the present document is to replace the natural crystalline lens. The implantation of the accommodative intraocular lens can be justified by the loss of transparency of the crystalline lens, as occurs with cataracts. Its use is also pertinent to the replacement of a crystalline lens that has lost the capacity to vary its power, as occurs in the development of presbyopia.

The intraocular lens for presbyopia correction of this invention pertains to the genus of accommodative lenses, inasmuch as it takes advantage of the contraction of the ciliary muscle to vary its power. Its design enables transforming contractions and stretching of the ciliary muscle on the order of few micrometers in power changes of various dioptres. These power changes are not produced as a consequence of a variation in the position of the lens with respect to the rest of the elements of the eye. There are no optical zones with distinct power that simultaneously generate distinct foci, as in the case of multifocal lenses. On the other hand, its design ensures that neither are there variations between the distance of the pieces that comprise it, but rather they remain fixed in relation to their relative position. Therefore, the intraocular lens presented in this invention does not belong to the species of simple optical pseudo-accommodative intraocular lens for presbyopia correction, the genus of compound optics, or of the multifocal lenses.

The subject intraocular lens of this invention belongs to the group of pseudo-accommodative lenses, although due to their novel design and operating principle, it is not possible to classify it in any of the two genera in this group.

The subject intraocular lens of this invention inaugurates a new genus within the pseudo-accommodative lenses which could be called of variable or accommodating power and fixed position. The invention provides a prosthesis that produces significant changes of optical or refractive power in the complete eye under the accommodative demand of the subject, with a simplified design, and which in turn enables implantation through corneal incisions of 2-3 millimeters or less.

The variable power accommodative intraocular lens comprises an optical zone, a substrate that surrounds said optical zone, holding it and capable of transmitting external forces, and a system of mechanical haptics, also called haptics, the bases of which are located on the substrate that surrounds said optical zone and which is capable of transmitting forces external to said substrate. The optical zone comprises at least four refracting interfaces, with a single common optical axis that separate at least three materials, with the adjacent materials having a different refraction index, the equatorial end of which is joined by said substrate. The materials that constitute the optical zone are flexible and capable of being deformed in response to external forces.

The novel design that is shown in the present invention makes it possible to take advantage of ciliary muscle contractions on the order of micrometers in order to produce changes in the optic power of the eye within the range of dioptres.

The substrate can adopt to different shapes. Its preferred embodiment is hexagonal for the simplicity of mechanical milling and its advantages for distributing forces inside it. There are other possible geometries for the contour of the substrate without loosing effectiveness. For example, a circular, octagonal, decagonal, dodecagonal, shaped substrate, etc., may be used. In general any regular polygonal shape is possible for the embodiment.

The optical zone of the lens has four different refracting interfaces, generated in index of refraction changing zones, corresponding to the different materials that can comprise the optical zone. The arrangement of these refracting interfaces constitutes what is commonly known in optical design as a triplet, because it is composed of three materials which may possibly be different. The substrate of the lens may coincide with one of the materials that comprise the optical zone. This may even be applied to the haptics, which may also be comprised of the material of the substrate itself.

The power change of the entire eye in response to the accommodative effort, when it has an intraocular lens implanted as described in this invention, is produced in connection with a change in the equatorial diameter of the optical zone of the intraocular lens. This variation brings about a redistribution in the thicknesses of the materials forming the optical zone. This same effect produces a change in the radii of the curvature of the four refracting interfaces that the intraocular lens presents. The combination of both changes, in curvature thickness and radii, is responsible for the power increase of the lens. One embodiment of the lens consists in employing the same material for the first and third material, while the centre is filled with a gas, air for example. This makes the central zone have a lower refraction index than the peripheral materials. However, there are other alternative embodiments which produce a similar effect that employ the opposite strategy: a central material with a higher index than those of the periphery. This great freedom of material is based on the possibility of combining different curvature radii in each of the four refracting interfaces, and constitutes a big advantage for the invention. Depending on the option chosen in the end for comprising the triplet, a relationship between equatorial compression or stretching will be obtained, and a different power generated.

To obtain this effect, the materials that comprise the optical zone must be sufficiently flexible in order to be deformed in response to an external force, either compression or centripetal, or expansion or centrifugal. In any event, they must be more flexible and have less resistance to deformation than the haptics. For the power of the subject intraocular lens of this invention to be sufficient, in the sense of providing the patient a state of emmetropia in long vision, different designs may be employed. The designs must also enable the deformation of the lens to be efficient by means of the change of its equatorial diameter. For this, the design must provide a power change linked to small changes in equatorial diameter. In a preferred embodiment of the invention, an arrangement of refracting interfaces is proposed where the anterior or first face, in the direction of the incident light from outside the eye, and a third face have a positive curvature radius. The posterior face or fourth surface and the second surface have a negative curvature radius.

In the preferred embodiment of the invention, three fasteners or haptics are employed. This raises manufacturing economy, while at the same time providing some good mechanical features regarding the capacity to transmit the centripetal or centrifugal forces to the intraocular lens. It is also possible to employ a larger number of haptics, such as four or six, for example. Increasing the number of haptics facilitates a better deformation with respect to the degree of homogeneity of the substrate. This is obtained at the expense of making the fold of the intraocular lens prior to its surgical implantation more complicated, which forces making larger corneal incisions.

The haptics have some special terminations and bases that enable their efficient operation. Essentially, the head is equipped with a system that absorbs small fluctuations in the equatorial diameter of the lens capsule, without transmitting them to the substrate. It also serves as an anchor when the intraocular lens is implanted together with a capsular tension ring. The latter constitutes the preferred embodiment of the invention. The base of the haptics is designed to efficiently compress the largest possible surface of the optical zone.

An alternative shape of the haptics design, called double headed, employs a pair of structural heads for a transmission of the external forces towards the optical zone of the lens. These double headed haptics must be implemented two by two, thus producing four contact points between the lens capsule or the capsular tension ring, and the structure of the intraocular lens.

The intraocular lens subject of the present invention may be implanted in the lens capsule of the patient directly, once the original crystalline lens that was inside it has been eliminated. In this modality the contraction of the lens capsule produced by the contraction of the ciliary muscle produces in turn a contraction of the equatorial diameter in the optical zone of the intraocular lens, which is responsible for the increase of power during the accommodation. The intraocular lens in the state of isolated balance is at its minimum power value or, equivalently, the far vision.

For the purpose of accurately controlling the force that is exercised on the intraocular lens, the preferred implementation of the invention is carried out by the combined use of a capsular tension ring. For this, the intracapsular ring is equipped with special anchors that are able to house the heads of the haptics. This way enables the haptics to be solidly fastened to the ring once they are implanted. The anchors for the heads of the haptics can be of various types, producing the same results. A possible embodiment of the anchors consists in some orifices that are visible from outside the eye, this being the normal aperture to the direction of the optical axis. Alternatively, the aperture may be on a parallel plane to the optical axis, in which case they would not be directly visible from the outside. Another alternative embodiment consists in anchors provided with magnetic properties. For the correct operation of this alternative, the heads of the haptics must be provided with magnetic properties. The capsular tension ring is provided with an aperture which includes some adjustable male/female terminations that define the minimum diameter that the ring can reach. The process for the practical implementation of the invention consists first in the implementation of the intracapsular ring in order to subsequently introduce the intraocular lens in the capsule. Afterwards, this must be appropriately anchored to the ring by means of the previously described haptics and anchors.

In the preferred embodiment of the invention, the intraocular lens in isolated state and in conjunction with an intracapsular ring has the maximum power, that is, it corresponds to the state of maximum accommodation. This is similar to what occurs with the human crystalline lens. Once the intraocular lens is anchored to the haptics of the intracapsular ring, the latter is left in a stretched state, in which it has a lower power than in the isolated situation. Upon implantation, the tension ring is in a position of maximum diameter, limited only by the capsule that contains it. In this way the capsule has a significant equatorial stretching that frees it from the tension exercised by the zonule, in such a way that the latter is not capable of transmitting any force to the capsule. When the anchoring of the heads of the haptics to the tension ring is produced, a centripetal force is created because of the elastic property of the intraocular lens, which reduces the diameter of the capsular ring. The capsule and the zonule return to recover their original states of far vision. In this situation, a change in the space between the ciliary muscle and the capsule, produced by a contraction of the ciliary muscle, also produces a release of the tension in the zonule, and consequently a contraction in the capsule. In this way the capacity of accommodative with the contraction of the ciliary muscle is returned, allowing the intraocular lens to increase its power when it approaches its isolated state.

BRIEF DESCRIPTION OF THE DRAWINGS

The following is a non-limiting illustration of the subject matter of the present invention, making reference to the drawings that accompany it, in which:

FIG. 4A corresponds to a spherical substrate design; FIG. 4B shows a regular decagonal profile; FIG. 4C has a regular dodecagonal.

FIG. 7A shows an optical zone with a large equatorial diameter and larger curvature radii with respect to FIG. 7B in all the faces or separation surfaces between the materials that comprise it. This corresponds to the lowest power state of the lens, or far vision. FIG. 7B shows an optical zone with a lower equatorial diameter and smaller curvature radii on all the faces or separation surfaces between the materials that comprise it, with respect to FIG. 7A. This corresponds to the higher power state of the lens, or near vision.

FIG. 8A corresponds to the preferred embodiment of the invention, which also shows an axis of sagittal symmetry. Both are found in the stretched situation or of the largest equatorial diameter, corresponding to far vision.

FIG. 10B shows an axis of sagittal symmetry. Both are found in the stretched situation or of the largest equatorial diameter, corresponding to far vision.

FIG. 12A shows a design that employs six haptics uniformly distributed in a radial shape over the hexagonal substrate, whereas FIG. 12B corresponds to another alternative embodiment with four haptics likewise arranged radially.

FIG. 13A is a perspective view of the element while FIGS. 13B and 13C show a front and lateral view, respectively. The haptic has three well differentiated zones, which are the head, trunk and base.

FIG. 14A is a perspective view of the element, while FIGS. 14B and 14B show a front and lateral view, respectively. The haptic has three well differentiated zones, which are the head, trunk, and a compound base that enables applying pressure simultaneously on two zones of the triplet of the intraocular lens.

FIG. 15A is a perspective view of the element, while FIG. 15B shows a front view.

FIGS. 19A, 19B and 19C correspond to the front, lateral, and top view of the piece, respectively. The structure is provided with an orifice that allows the full insertion of the head of the haptic.

FIGS. 20A, 20B and 20C correspond to the front, lateral, and top view of the piece, respectively. The structure is provided with an orifice that allows the full insertion of the head of the haptic, and is oriented parallel to the optical axis of the eye.

DETAILED DESCRIPTION OF THE INVENTION

The present invention consists in a lens and its corresponding haptics designed for its implantation in human eyes. Its purpose is to replace the natural crystalline lens, especially in those situations in which the it does not fulfil its physiological functions correctly. This may happen basically for three causes, which are explained as follows: lack of transparency; incapacity of the crystalline lens to change its power or refractive power in the accommodation of the vision to different distances; an inadequate optical power along the axial length of the full eye. This latter is the cause of ametropias in the vision of the patient, such as myopia, hyperopia or astigmatism when they are considered powers dependent on the meridian.

Figure 1:
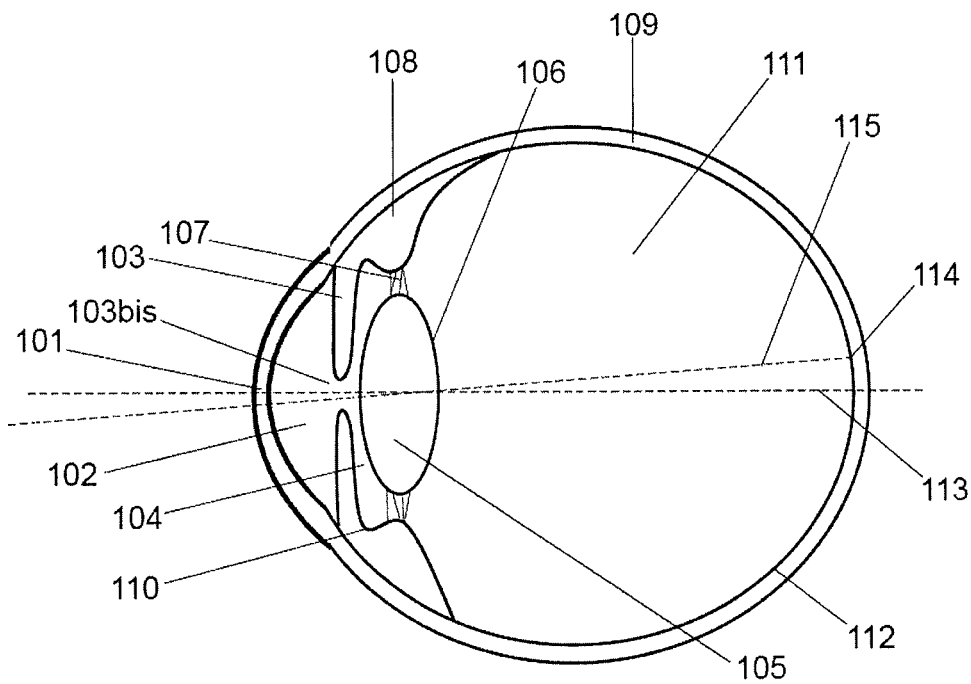
FIG. 1 schematically shows the shape of the fundamental parts that comprise the human eye by means of a horizontal section of it. The figure presents those portions of the eye that are of interest for the invention, and includes the elements involved in the process of accommodation. The most important axes of the eye are shown with dotted lines.

For the purpose of facilitating the understanding of the invention, FIG. 1 shows the schematic shape of the fundamental portions that comprise the human eye by means of a horizontal section of it. Specifically, said figure presents those parts of the human eye that are relevant for the invention, and includes the elements involved in the process of accommodation. The most important axes of the eye are shown with dotted lines.

The eye is a complex organ that has a great histological richness. In the first place, the light coming from an external scene passes through the cornea 101, which provides the eye with approximately two thirds of the total optical power. For optical purposes, its characterisation is made with the radii of the curvature of the anterior and posterior faces, its thickness and its index of refraction, which has an average value of 1.38. Behind the cornea 101 is the anterior chamber 102, a space full of aqueous humour, which is essentially composed of water, with an average thickness of 3.05 millimeters and an index of refraction of 1.34. The light next encounters the iris 103, a circular muscle that defines an aperture or pupil 103*bis*, through which the light enters the rest of the eye. The diameter of the pupil 103*bis* changes physiologically, among other reasons in response to variations in the illumination of the scene and changes in the distance to the point of fixation. Behind the iris 103, in the direction of the entering light, is the posterior chamber 104, also full of aqueous humour. The limit of the posterior chamber 104 is the crystalline lens 105. Without a doubt, this is one of the most delicate and complex elements of the eye. It provides the eye, together with the cornea 101, the refractive power necessary for forming sharp images on the retina 112 of the subject. The crystalline lens 104 is made up of a multitude of concentric caps with a different thickness and cellular age, which provides it with a complex index of refraction distribution along the length of its optical axis 113. Its exterior shape is biconvex, slightly more curved on its posterior face, and has a total average thickness of four millimeters. For its study and modelling, a single effective index of refraction value of 1.4 is usually adopted. The crystalline lens 105 is housed inside a fine membrane with elastic properties, basically comprised of type IV collagen, known as the capsule 106. The stiffness of the capsule 106 in a young eye is greater than that of the crystalline lens 105, and therefore determines the exterior shape or profile of the latter. The lens capsule 106 is suspended along the equator by means of a fine network of elastic fibres known as zonule 107. At the exterior end, the zonule 107 is inserted through the ciliary processes in the ciliary muscle 108. This is already in contact with the outermost layer of the eye, the sclera 109. The ciliary muscle 108 defines a small invagination in the equatorial portion of the posterior chamber 104, known as the ciliary sulcus 110. All of these described elements, 106, 107, 108 are in some way connected to the crystalline lens 105 and are very relevant for understanding the process of accommodation, as will be shown further on. Behind the crystalline lens is the vitreous humour 111, having a gelatinous composition with an index of refraction similar to aqueous humour that maintains the parts of the eye in their correct position and protects the retina 112. The retina 112 is formed by a multitude of different classes of cells, with a very sharp segregation in the layers. The transduction of the optical image that is projected on it is done in its core, with impulses and signals that are sent to the brain through nerve cells for decodification and subjective interpretation, thereby completing the phenomenon of vision. For the study of formation of images in the eye, it is useful to define some axes. On the one hand, the optical axis 113, as the one that approximately has the approximate centres of curvature of the different surfaces that comprise the eye. The zone of the retina 112, where the central vision is made, known as the fovea 114. In the eye the optical axis in general does not pass through the fovea 114. Therefore, the visual axis 115 is defined as the imaginary axis that joins the fovea 114 to the point of fixation of the gaze. The angle that forms the optical axis 113 and the visual axis 115, is known as the alpha angle.

Figure 2:
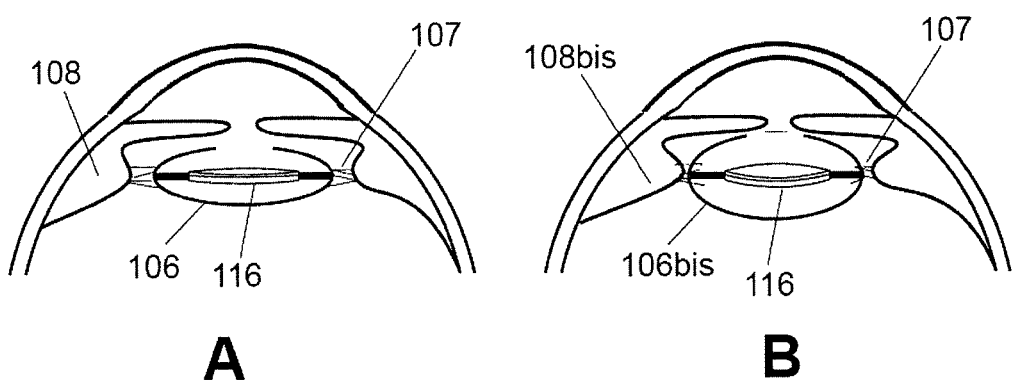
FIGS. 2A and 2B show a schematic view of the process of accommodation of the human eye once the intraocular lens has been implanted. For this, the figures only show the portions of the eye involved in this process. Two horizontal sections are shown, corresponding to the anterior portion of the eye, or the closest to the exterior. The situation of the unaccommodated eye or far vision is sown in FIG. 2A, and the accommodated eye or near vision in FIG. 2B.
Figure 4:
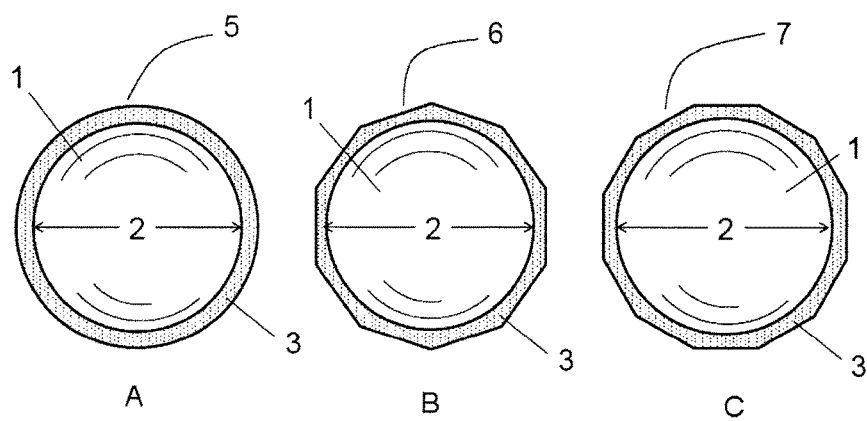
FIGS. 4A, 4B and 4C show schematically some front views of the variable power intraocular lens subject of the this invention, where both the substrate and the optical zone of the lens have different alternative shapes. The haptics are not shown.

FIGS. 2A and 2B show a schematic view of the process of accommodation of the human eye once the intraocular lens 116 has been implanted. The intraocular lens 116, subject of this invention, is designed to be implanted in the lens capsule 106. To do so, the intraocular lens 116 is introduced through the orifice that enables the evacuation of the crystalline lens 105 from the lens capsule during the surgical operation. The position of the intraocular lens 116 inside the eye is shown in FIGS. 2A and 2B. Once in place inside the lens capsule 106, the intraocular lens 116 has the capacity to vary its geometric parameters and, consequently, its optical power. The variations of power in the intraocular lens 116 are produced as an indirect consequence of the contraction 108*bis* and stretching of the ciliary muscle 108 during the process of accommodation. The changes in the ciliary muscle translate into a stretching 106 or contraction of the lens capsule 106*bis*, which produces the resulting change on the intraocular lens 116. In the situation of far vision (FIG. 2A) the intraocular lens 116 and the lens capsule 106 are stretched, reaching a maximum equatorial diameter. The zonule 107 transmits the tension to the capsule, induced by the stretching to which it is submitted due to the relaxing of the ciliary muscle. In near vision (FIG. 2B), the intraocular lens 116 and the lens capsule 106, tend towards their relaxed state, thanks to the lower tension exercised by the zonule 107 on the lens capsule. The latter loses its tension due to the contraction of the ciliary muscle 108, which reduces the space around the lens capsule on its equatorial plane. The intraocular lens 116 shows a lower equatorial diameter, while the curvatures of the anterior and posterior faces of these elements increase The Intraocular Lens The variable power intraocular lens 116, subject of this invention, is designed for surgical implantation inside the lens capsule 106 in human eyes in the place of the natural crystalline lens 105, previously eliminated. The lens 116 has an optical or refractive zone 1, preferably with a circular shape, as FIG. 4A shows, having a useful optical diameter 2 that takes values between 5 and 6 millimeters, ideally 6 millimeters. This optical zone 1 must have a sufficient diameter for allowing the passage of light coming from the exterior towards the retina. Otherwise, halos could appear, particularly when the pupil 103*bis* of the eye is in a mydriatic or dilated condition caused by the low illumination on the scene. The optical zone 1 is responsible for the refractive power or power of the intraocular lens 116. The change in the equatorial diameter of the optical zone 1 is responsible for the variation of the power in the intraocular lens 116.

Figure 3:
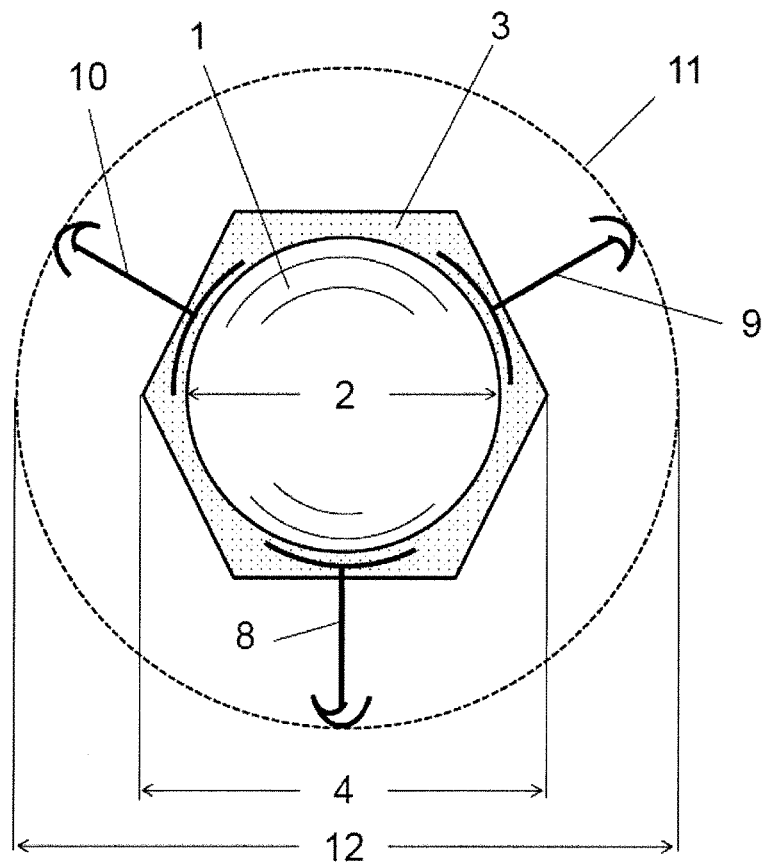
FIG. 3 shows the preferred embodiment of the variable power intraocular lens with a front view of it. The optical zone in its central area is shown, with the surrounding substrate that has a hexagonal shape, and three haptics or haptics responsible for holding it centred.

There is a substrate or frame 3 surrounding the optical zone 1, with the purpose of holding it in place. In an optimal design, this substrate 3 has an external hexagonal shape, as FIG. 3 shows. The external hexagonal polygonal shape of the fastening substrate 3 in the preferred embodiment of the intraocular lens 116, may be considered inscribed in a circumference 4 having a diameter between 5.5 and 7.5 millimeters, and an ideal size of 7 millimeters. Its equatorial thickness must be sufficient for holding against the optical zone 1 and, nevertheless, maintaining the capacity to be deformed by the external radial pressures. This regular polygon shape provides the advantage, thanks to its edges, of braking the migration of epithelial cells towards the posterior face of the lens capsule 106. On some occasions this cell migration produces the opacification or loss of transparency of said face. This effect may possibly be so pernicious that it makes an intervention necessary to clean it, for the purpose of recovering the transparency needed for correct vision.

Figure 6:
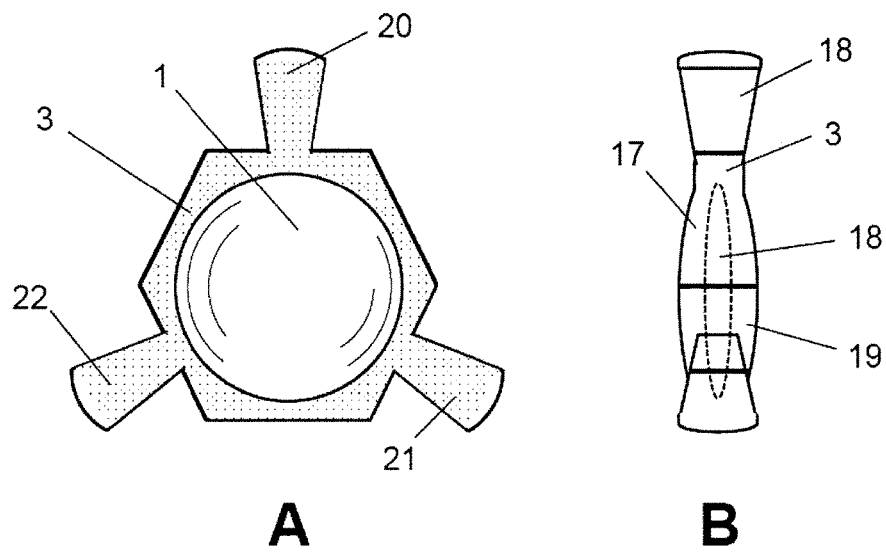
FIG. 6A shows a front view of an alternative embodiment of the variable power intraocular lens, in which the haptics or fasteners are made of the same material as the substrate.
FIG. 6B shows a lateral view of the design.
Figure 7:
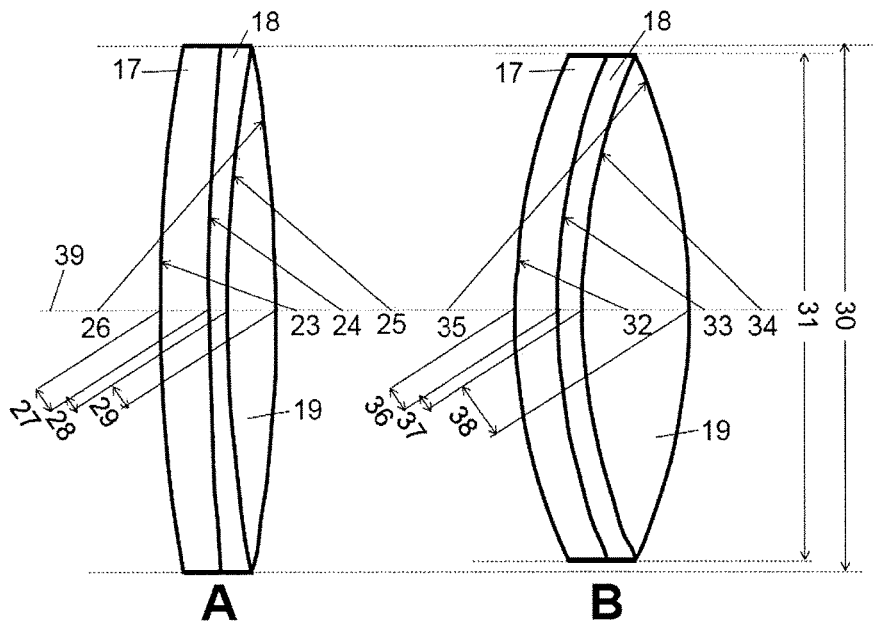
FIGS. 7A and 7B show two sagittal sections of the optical portion of the intraocular lens subject of this invention in its preferred embodiment having the optical triplet structure.

Other geometrical shapes of the substrate 3 may be employed in the practical embodiment of the intraocular lens 116, with a similar result, as FIGS. 4A, 4B and 4C show. For example, the circular shape 5 for the substrate 3 may be useful in certain situations, because it enables simpler manufacturing, and the centripetal pressures on the optical zone 1 needed so that its change of power can be distributed in a more uniform manner. However, it does occur that the circular shape on the perimeter of the intraocular lens 116 does not break the migration process of epithelial cells towards the posterior face of the lens capsule 106 in as efficient a way as those lenses provided with an edge on their external border. In this regard, other geometric shapes of the substrate 3 based on inscribed regular polygonal FIGS. 6, 7 on a circumference are more advantageous. As alternatives for illustrating that design possibility, aside from the preferred hexagonal polygonal proposal of FIG. 3, a substrate is shown having an external shape that corresponds to a decagon 6 and another with a dodecagon shape 7 (FIG. 4C)

The intraocular lens 116 is provided with some mechanical supports or haptics that enable it to remain in a centred position inside the lens capsule 106 with respect to the optical axis of the eye. The preferred arrangement of the haptics 8, 9, 10 is shown in FIG. 3. These are placed occupying the position of the angle bisectors of a virtual equilateral triangle having a centre on the optical axis of the intraocular lens 116, inscribed on a circumference 11 of diameter 12 between 9.5 and 12 millimeters, ideally 10.5 millimeters. The haptics are partially embedded in the substrate 3. In this way they maintain their position and are capable of transmitting the external forces necessary for the deformation of the lens 116 in an efficient manner.

Figure 5:
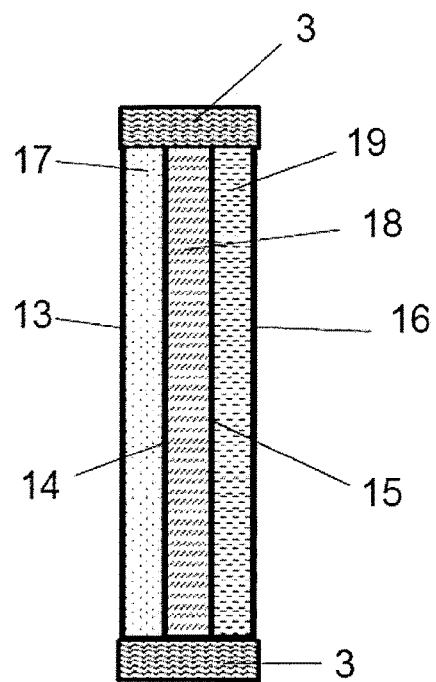
FIG. 5 schematically shows the composition in regards to the materials of the internal structure of the optical zone and the substrate of the intraocular lens subject of this invention. The figure presents a sagittal section of the lens. The substrate, the top and bottom horizontal portion, and the triplet that shapes the optical zone are shown clearly differentiated. The latter is comprised of three materials from which originate the four refracting interfaces.

A sagittal section of the intraocular lens 116, FIG. 5, enables showing schematically the internal arrangement of the different materials and of the substrate that shapes it. The intraocular lens 116 is comprised of four refracting interfaces 13, 14, 15, 16 which are shaped as a consequence of the changes in the index of refraction, and which are introduced on the path of the light towards the retina. In this way it may be considered that the intraocular lens 116 forms what in optics is known as a triplet type lens surrounded equatorially by a substrate 3. The first refracting surface 13 in the direction of the incident light from the exterior is formed in the separation zone between the aqueous humour that completely fills the lens capsule 106 once it has been evacuated of its crystalline lens 105, and the anterior material 17 that comprises the optical zone 1 of the intraocular lens 116. The second refracting surface 14 already separates the first two materials, the anterior 17 and the central 18, which have different refraction indexes. The central materials 18 and posterior 19 have the third refracting surface as effective separation 15. Finally, the fourth and last refracting surface 16, serves as the border between the posterior material 19 and the aqueous humour. All of the materials involved in the intraocular lens 116 (3, 17, 18, 19) of the previous description may be different. A preferred embodiment of the invention proposes an arrangement in which the central material 18 is a gas, preferably air. In the preferred realization the anterior material 17 and posterior material 19, as well as the one forming the substrate 3, are the same. In this manner an easily manufactured intraocular lens 116 that maintains the advantages of a triplet is obtained. FIG. 6A shows an embodiment of the invention that incorporates the previously described concept of a single material. FIG. 6B is a lateral view of the design. The central element of the triplet 18 shows a cavity for being occupied with gas, preferably air. That portion of the triplet may be filled with gas once the intraocular lens 116 has been implanted in the lens capsule 106. That may be done during the same surgical intervention for eliminating the natural crystalline lens 105 and implanting the intraocular lens 116, or in a later intervention. The filling of the central cavity of the triplet may be carried out by employing a syringe that insufflates the gas once an orifice has been made through the anterior face of the triplet 17, or preferably of the substrate 3, with a needle. This needle must have a small diameter so the alteration of the structure and biomechanical properties of the triplet is minimal. The amount of gas needed to comprise the correct power of the triplet must have been calculated beforehand. For this, in practice the syringe for the insufflation of the air must be pre-loaded with the necessary volume for adequately carrying out the operation. Another alternative that may be interesting in certain cases, is adjusting the power of the lens 16 in real time by controlling the volume of the insufflated gas during the intervention or after it. For this a measurement of the eye refraction in real time and simultaneously with the operation is required. At present, the state of the art enables this modality through wavefront sensors, such as, for example, a Hartmann-Shack sensor. Thus, the curvature radius of the four refracting interfaces that comprise the triplet and the thickness of each one of the materials forming it, may be controlled by the injection of more or less gas. This alternative may be particularly interesting in those eyes where the calculation for obtaining the power of the intraocular lens 116 to be implanted was done incorrectly. This is a relatively frequent case in those patients who prior to the cataract operation or, in general, to the operation to change the crystalline lens 105 for an intraocular lens 116, have undergone a refractive surgical operation by carving the cornea using any of its variants, such as LASIK or LASEK. In these cases the standard biometrics that are made do not produce reliable data on the shape and power of the cornea for the subsequent calculation of the intraocular lens 116.

A feature of the design shown in FIGS. 6A and &B, is that the haptics 20, 21, 22, are also formed with the same material as the substrate 3 and the anterior face 17 and the posterior face 19. That gives the lens 116 an additional advantage in terms of simplicity and cost during the manufacturing process.

The intraocular lens 116 may also incorporate the correction of astigmatism as needed by each subject. The correction of astigmatism is routinely done with ophthalmic lenses and contact lenses with what is known as toric surfaces. For the correction of astigmatism with the intraocular lens 116, subject of this invention, one of the four surfaces comprising the triplet may incorporate a different power depending on the meridian considered. Another alternative manner is to carve two or more surfaces with astigmatism values in a way that the combination of all of them produces the necessary value for compensating the astigmatism of the patient. Due to the directional character of astigmatism, it is necessary to implant the lens in a way that its final placement guarantees the axes coincide with the astigmatism of the patient. This may be done in practice simply by marking the substrate so that the indicator is visible to the surgeon, who may change the angular position of the lens during the operation.

The intraocular lens 116, subject of the present invention, may be provided with aspheric surfaces for the correction or induction of higher order aberrations than blurring and astigmatism. This is obtained by the corresponding carving of any of the four refracting interfaces comprising lens 116. Just as was explained in the case of astigmatism, it is also possible to carve the profiles on two or more surfaces simultaneously so that the combination of all of them produces the desired result. Thus, the aberrations pertaining to the eye of the patient may be incorporated in the intraocular lens 116 with the opposite sign. In this way the combination of the aberrations of the intraocular lens 116 and those of the patient, produce a wavefront that is practically free of optical aberrations, which results in an optical quality of the image that is projected on the retina limited by the diffraction of the pupil. The optical aberrations of the subject may be completely corrected, or just some of the most significant terms, such as, for example, spherical aberration. This aberration is important in the eyes of elderly patients, as well as in patients who have previously undergone refractive surgery by carving the cornea.

Another possibility linked to carving high order aberrations in one or several of the surfaces comprising the intraocular lens 116, is the generation of phase profiles that increase the depth of the field of the patient.

The intraocular lens 116, subject of this invention, may also be provided with a pupil. For this, the materials comprising it may be painted or stained using different methods for generating an aperture with the required placement and sizes. The priming may be done on one of the faces or refracting interfaces, or several of them may be stained simultaneously, obtaining the same effect. This manner of actuating on the light is commonly known as amplitude modulation, or apodization. The creation of a small pupil can notably amplify the field depth, as is well known in the field of imaging. This can be taken advantage of for improving the quality of the retinal images at different distances. This amplification of field depth can also be generated by modulating the amplitude with profiles specifically designed to do so, in a way similar to how it is done by actuating on the phase amplitude. The chromatic aberration of the eye can also be fully corrected with amplitude modulation, as shown in the document of A. Márquez, C. Iemmi, J. Campos, J. Escalera, and M. Yzuel, "Programmable apodizer to compensate chromatic aberration effects using a liquid crystal spatial light modulator," Optics Express 13, 716-715 (2005).

The Change of Power in the Intraocular Lens

The design advantage of the intraocular lens 116 that is described in the present invention, with respect to the already existing ones, is its large capacity for changing the power in response to small changes in the equatorial diameter. For viewing nearby objects, it is necessary to increase the power of the intraocular lens 116. Starting from this situation of near vision, the lens 116 must also be capable of decreasing its power when the object, the point of fixation, moves away from the subject. The intraocular lens 116 of this invention employs the mechanical forces originating in the ciliary muscle to adapt its power. In this way it is possible to obtain a sharp image of the object on the retina in a broad range of distances from the eye. The contractions and relaxing of the ciliary muscle produce tension changes in the zonule 107, which are transmitted to the lens capsule 106. The intraocular lens 116 takes advantage of these tension changes in the lens capsule 106 to vary its power.

The mechanism that causes the intraocular lens 116 to change its power is the variation of its equatorial diameter. Specifically the equatorial diameter in the optical zone 1. Thus, the materials comprising the triplet in the intraocular lens 116 (17, 18, 19) must be sufficiently flexible and elastic to carry out this operation correctly. On the one side, they must have little resistance to the deformation, and on the other, they must be capable of returning to their relaxed state once the effects of the external forces have ceased. The current state of the art provides adequate materials that meet these properties.

The present section will centre on the optical zone 1, as responsible for the change in power of the intraocular lens 116, once the external focuses have been adequately transmitted to it. For this, it has a specific system of haptics, which will be described in another section of the document.

The design of the intraocular lens 116 guarantees that the variation of the equatorial diameter causes a change of the curvature radii of the refracting interfaces comprising the triplet 13, 14, 15, as well as a change of thickness in each of the materials comprising it (17, 18, 19). FIGS. 7A and 7B show clear equatorial sections of the optical zone 1 of the intraocular lens 116, corresponding to the far vision (FIG. 7A) and the unaccommodated situation or near vision (FIG. 7B). The design of the lens 116, as regards its optical zone, is perfectly described when the materials comprising it 17, 18, 19 are specified, together with the geometric parameters that are relevant for its refractive power. The latter are the radii of curvature of the anterior face 23 and posterior face 24 of the first material 17, and the corresponding anterior ratio 25 and posterior ratio 26 of the last material 19 of the triplet. The central thicknesses 27, 28, 29 of each of the materials comprising it 17, 18 19, are also necessary geometric parameters for the characterisation of the triplet. The equatorial diameter 30 of the lens 116 completes the description from an optical point of view of the triplet. In far vision this equatorial diameter 30 is superior to the situation of near vision 31. FIGS. 7A and 7B show a net change of the equatorial diameter of 2.12% over an initial diameter of 5.5 millimeters. This represents an equatorial contraction of 110 micrometers in the lens 116 of FIG. 7B.

Table 1 shows the optical and geometrical parameters that define the design of various triplets shown in FIGS. 7A and 7B, FIGS. 8A and 8B, and FIGS. 10A and 10B. The parameter include the refraction indexes ($n_1$, $n_2$, $n_3$) of each of the materials comprising the triplet, the curvature radii ($R_1$, $R_2$, $R_3$, $R_4$) of each of the refracting interfaces, the thickness of the materials ($d_1$, $d_2$, $d_3$) and the diameter ($D_1$) of the optical zone in the stretched situation or far vision.

TABLE 1

Figure 8:
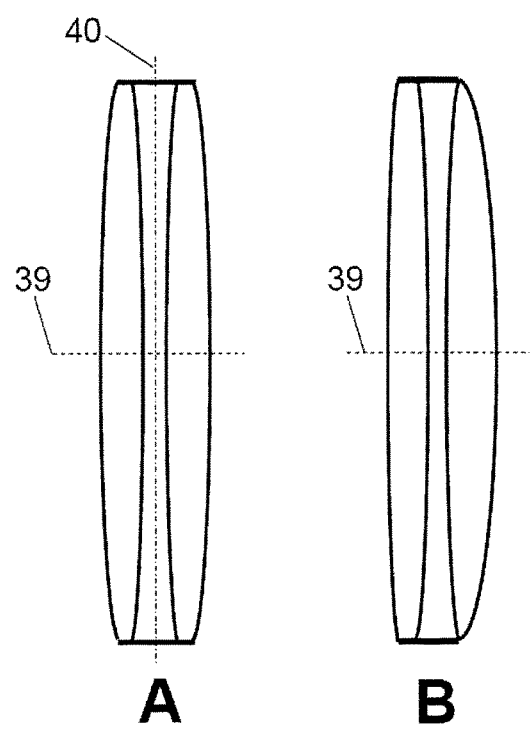
FIGS. 8A and 8B show sagittal sections of the optical zone with two different designs that produce a similar effect.

| | $n_1$ | $n_2$ | $n_3$ | $R_1$ | $R_2$ | $R_3$ | $R_4$ | $d_1$ | $d_2$ | $d_3$ | $D_1$ |
|---|---|---|---|---|---|---|---|---|---|---|---|
| FIG. 5A | 1.41 | 1.00 | 1.41 | 16.23 | 26.75 | 15.46 | −16.23 | 0.50 | 0.20 | 0.50 | 5.50 |
| FIG. 6A | 1.41 | 1.00 | 1.41 | 48.64 | −48.64 | 48.64 | −48.64 | 0.45 | 0.25 | 0.45 | 6.00 |
| FIG. 6B | 1.41 | 1.00 | 1.41 | 50.00 | −62.29 | 62.29 | −15.00 | 0.40 | 0.20 | 0.40 | 5.70 |
| FIG. 8A | 1.50 | 1.00 | 1.50 | 59.81 | 27.00 | 15.00 | −59.81 | 0.40 | 0.35 | 0.40 | 6.00 |
| FIG. 8B | 1.41 | 1.50 | 1.41 | 11.31 | 27.00 | −27.00 | −11.31 | 0.30 | 0.35 | 0.30 | 6.00 |

With the geometric parameters of this lens 116, shown in Table 1, this contraction introduces a total increase of the power of the eye of about 4 dioptres. To obtain this estimate, an optical eye model described in the work of Liou and Brenan is used [Liou and Brennan, "Anatomically accurate, finite model eye for optical modeling," Journal of the Optical Society of America A 14, 1684-1695 (1997)]. When the equatorial diameter of the lens 116 is lower (31) a series of changes are produced in all the geometric parameters of the triplet that are directly responsible for the power change. The curvatures (32, 33, 34, 35) of each and every one of the surfaces increase. The central thicknesses (36, 37, 38) undergo changes that depend on the sign of the curvature radius of the refracting interfaces that limit the material. The design of FIG. 7B, as an example, the third material 19 undergoes an increase in its central thickness 38, due to the initial curvature of the refracting interfaces that limit it 25, 26 in response to the contraction around the optical axis 39 of the lens 116. These initially form a biconvex lens. In the case of a biconvex lens, the situation would be the opposite when faced with a contraction in the equatorial diameter of the lens 116, and the central thickness would undergo a decrease. In the case of convex-concave or concave-convex lenses, the variation in the central thickness, its increase or decrease of the central thickness, has to be estimated based on the initial values of the curvature radii of the refracting interfaces that limit it.

Figure 10:
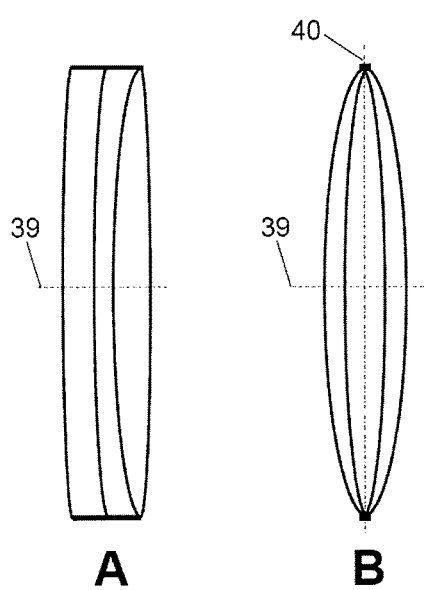
FIGS. 10A and 10B show sagittal sections of the optical zone with two different and alternative designs to the preferred embodiment of the invention that produce a similar effect.

Other variations and designs for the optical zone 1 of the intraocular lens 116 are possible based on the same concept as the lens 116 of the triplet type, the power of which can vary depending on the equatorial diameter. FIGS. 8A and 8B show a pair of designs that produce a larger power variation in response to small equatorial compressions. All of them prefer the use of the same material for the first and the third lens that comprise the triplet. Thanks to this fact, the advantage of a simpler and more efficient industrial production from the economical point of view is maintained. The use of larger curvature radii for the anterior and posterior faces produces a notable effect on the amount of contraction or stretching required to generate the same amount of power change. From this point on in the document, the ratio between the increase of power of the optical zone of the lens 116 and its equatorial contraction will be called the refractive power gain. FIG. 10A shows a schematic view of a design based on the one that appears in FIG. 7A with larger radii on the anterior and posterior faces. Another variation in the design that maintains similar properties of power change, is the one in which the optical zone of the intraocular lens 116 is symmetrical with respect of a central axis 40. Examples of this design are shown in FIG. 8A and FIG. 10B. The triplet in FIG. 10B employs as central material a silicone or similar material that provides a higher refraction index than the means surrounding it. A variation based on this idea, which produces an equal effect and technical advantages, is shown in FIG. 8A, a case in which the central material is air. An alternative to the lens 116 described in FIG. 8A, is the asymmetric triplet shown in FIG. 8B. This alternative design maintains the central portion filled with air, but is provided with more curvature on the posterior face than the anterior, thereby emulating the geometric shape of the natural crystalline lens 105. The geometric parameters which completely describe all the lenses 116 shown in FIGS. 8A, 8B and FIGS. 10A and 10B, are grouped together in Table 1. The table gives the curvature radii of each of the refracting interfaces ($R_1$, $R_2$, $R_3$, $R_4$), the thicknesses of the materials ($d_1$, $d_2$, $d_3$), their indexes of refraction ($n_1$, $n_2$, $n_3$), and the equatorial diameter of the optical zone ($D_1$).

Figure 9:
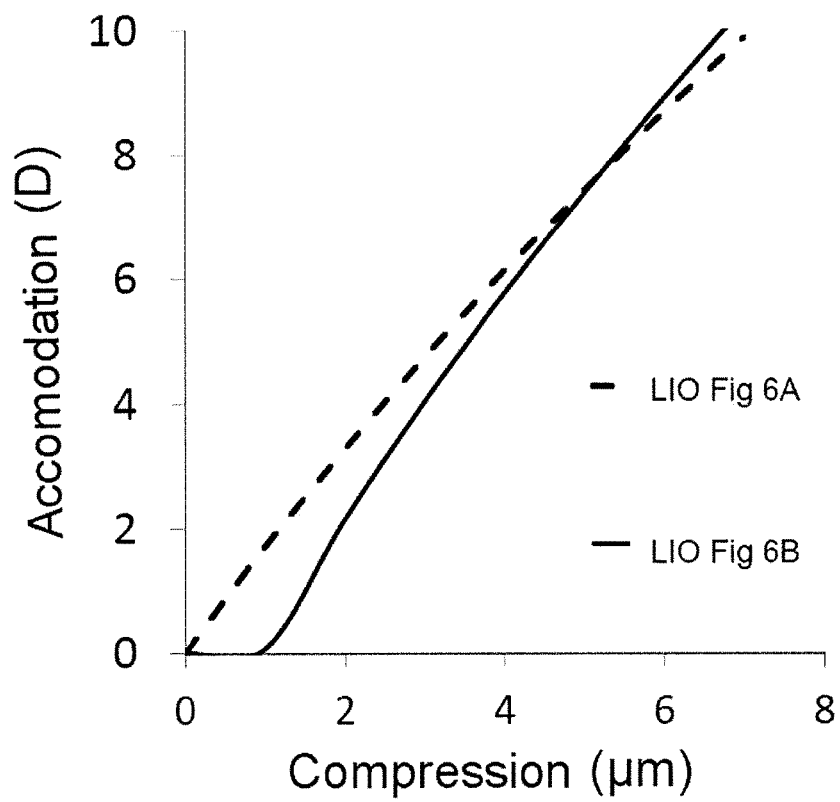
FIG. 9 shows the gain in refractive power corresponding to the different designs of the triplets that shape the optical zone of the intraocular lens subject of this invention shown in FIGS. 8A and 8B. The gain is expressed as the accommodation or increase of power, in dioptres, that the full eye experiences with the implanted intraocular lens when the equatorial diameter of its optical zone is compressed, in micrometers.
Figure 11:
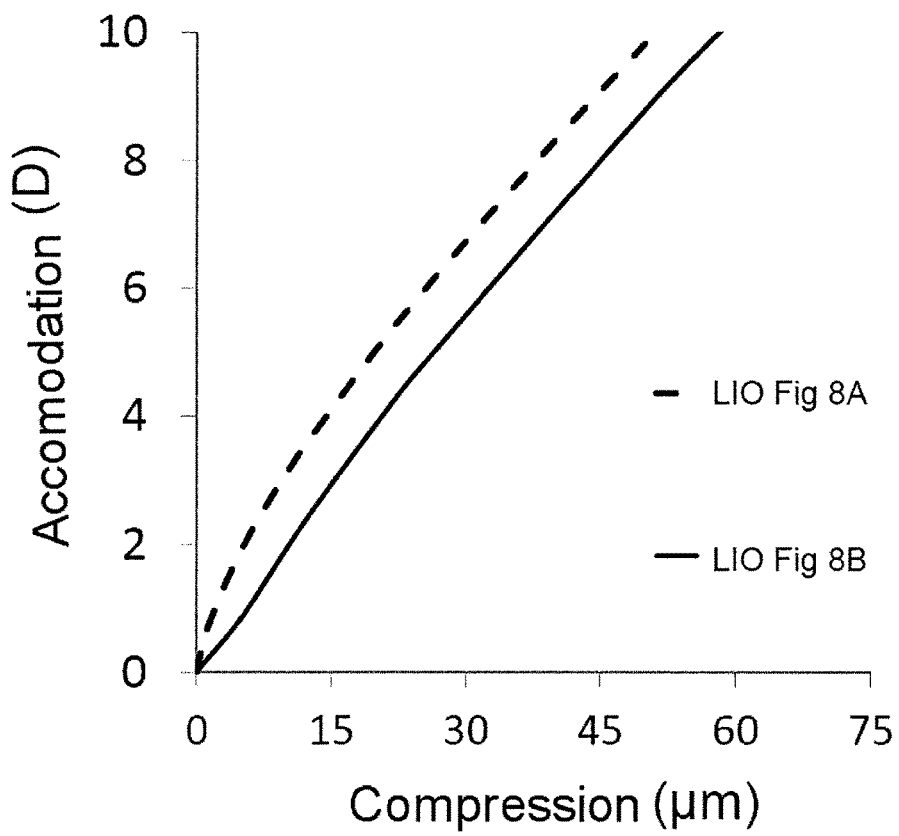
FIG. 11 shows the gain in refractive power corresponding to the different designs of the triplets that shape the optical zone of the intraocular lens subject of this invention shown in FIGS. 10A and 10B. The gain is expressed as the accommodation or increase of power, in dioptres, that the full eye experiences with the implanted intraocular lens when the equatorial diameter of its optical zone is compressed, in micrometers.

The age of the patient may determine the magnitude of the contraction of the ciliary muscle. Other factors such as the equatorial space around the crystalline lens 105 or the size of the lens capsule 106 itself, may also determine the maximum deformation that the intraocular lens 116 is going to experience during the accommodation. Different designs of the optical zone 1 of the intraocular lens 116 produce significant differences in the refractive power gain of the intraocular lens 116. FIG. 9 and FIG. 11 show the corresponding gains in the designs shown in FIGS. 8A, 8B and FIGS. 10A, 10B, respectively. FIGS. 9 and 11, show the changes in the total power of an emmetropic eye in dioptres (D) implanted with each of the previously described intraocular lenses 116. The changes in power are given exclusively by the equatorial contraction of the optical zone of the implanted intraocular lens 116. In FIGS. 9 and 11, the contraction of the intraocular lens 116 is shown as a net reduction of its diameter in micrometers (μm). For the designs proposed in FIGS. 8A and 8B, an equatorial contraction of just four micrometers produces an increase in power of the eye greater than four dioptres. Due to its efficient design, even eyes with a modest capacity to accommodate can produce significant changes in their power. For this reason the design shown in FIG. 8A is proposed as the preferred embodiment of the invention. This equals the sharp vision of objects located 10 centimeters from the eye. The design in FIG. 10A needs 14 micrometers of contraction to produce the same accommodation. With a value of 12 micrometers, the design of FIG. 10B, also attains four dioptres. The intraocular lens 116 that needs the greatest equatorial contraction for generating this example value of four dioptres is shown in FIG. 7A. In this last lens 116, 110 micrometers are needed to attain that value.

Haptics and Supports of the Intraocular Lens

Figure 12:
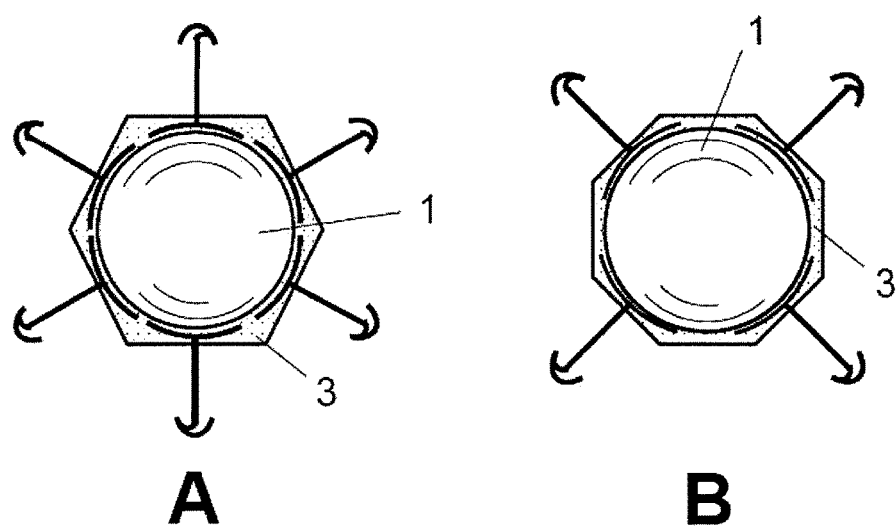
FIGS. 12A and 12B show alternative designs of the preferred embodiment as regards the distribution of the haptics or fasteners of the intraocular lens subject of the invention.
Figure 13:
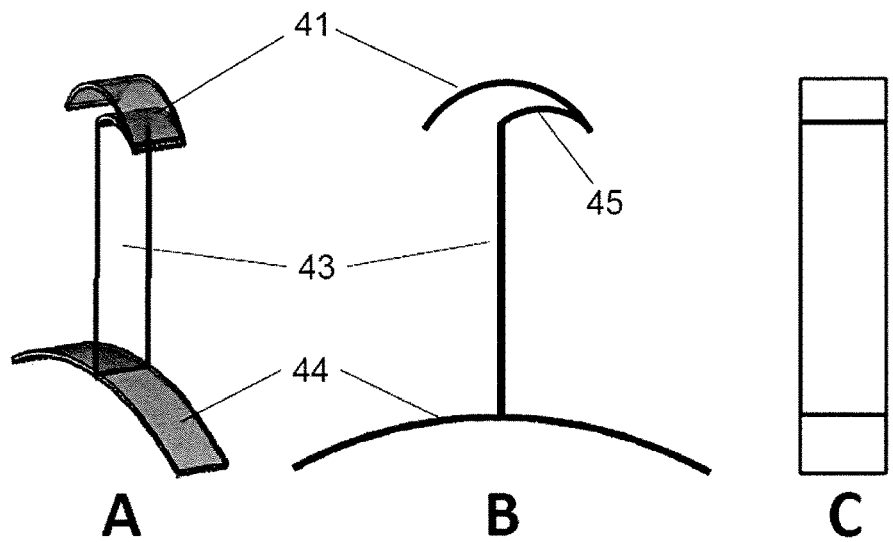
FIGS. 13A, 13B and 13C show in detail the structure of an isolated haptic or fastener in its preferred embodiment.

The fasteners or haptics of the intraocular lens 116 are a fundamental part of the design. Their most prominent property must be to transmit the force applied from the ciliary muscle to the optical zone 1 of the intraocular lens 116. As has been described above, the change of the power of the intraocular lens 116 is directly connected to the variation of its equatorial diameter. FIG. 3 shows a preferred embodiment of the invention, with 3 by 3 hexagonal substrate haptics. An alternative embodiment of the invention is shown in FIG. 12A. In this figure a new hexagonal substrate is employed, but provided with six haptics. The haptics are arranged in a regular manner, coinciding with the median line of each of the edges that comprise the hexagon. In this way the centripetal or centrifugal forces can be transmitted more efficiently to the optical zone 1 of the intraocular lens 116. FIG. 12B shows another alternative embodiment of the invention, this time with an octagonal substrate. Taking advantage of the arrangement of edges in this last shape, the use of four haptics is proposed for transmitting the force to the optical zone 1. The haptics shown in FIG. 3 and FIGS. 12A and 12B are made of a material that provides greater stiffness than the substrate 3 and the optical zone 1. In this way the haptics can deform the optical zone 1 without experiencing appreciable changes in their shape. The haptics can be incorporated into the intraocular lens 116 while in its mould during the silicon injecting process or, in general, of the material chosen for the substrate 3, thereby facilitating its mass production. FIGS. 13A, 13B, and 13C show the structure of an isolated haptic. FIG. 13A is a perspective view of the haptic, while FIGS. 13B and 13C show the plan and lateral view of it, respectively. The haptic uniformly distributes the pressure on the triplet that forms the optical portion 1 of the intraocular lens 116. The tension must be distributed on each of the materials (17, 18, 19) that comprise the lens 116, so that they can be deformed uniformly. The haptic consists of three well differentiated parts. The most external part, or head of the haptic 41, is designed to remain in contact with the lens capsule 106, or be anchored to a capsular ring 42, designed for that purpose. Preferably it has a half-moon shape. The following fundamental portion of the haptic is the trunk 43. This zone unites the head in contact with the substrate 3. Finally, there is the base 44, which comes already embedded in the substrate 3 and is responsible for uniformly distributing pressure on the different materials 17, 18, 19, that comprise the triplet. The thickness of the base must be sufficient to remain in simultaneous contact with the three zones 17, 18, 19 or materials forming the triplet. The union of the head 41 with the trunk 43 in the haptic is done by means of a type of bridge shaped like a half moon 45. This design enables the compression of the space between the head 41 and the joining bridge 45, without the force initially being transmitted to the trunk. In this way the haptic is provided flexibility for when it is accommodated inside the capsule 106 or anchoring itself to the capsular tension ring 42. This feature enables the correct use of the haptics without the need of first carrying out very precise biometric measurements of the equatorial diameter of the capsule 106.

Figure 14:
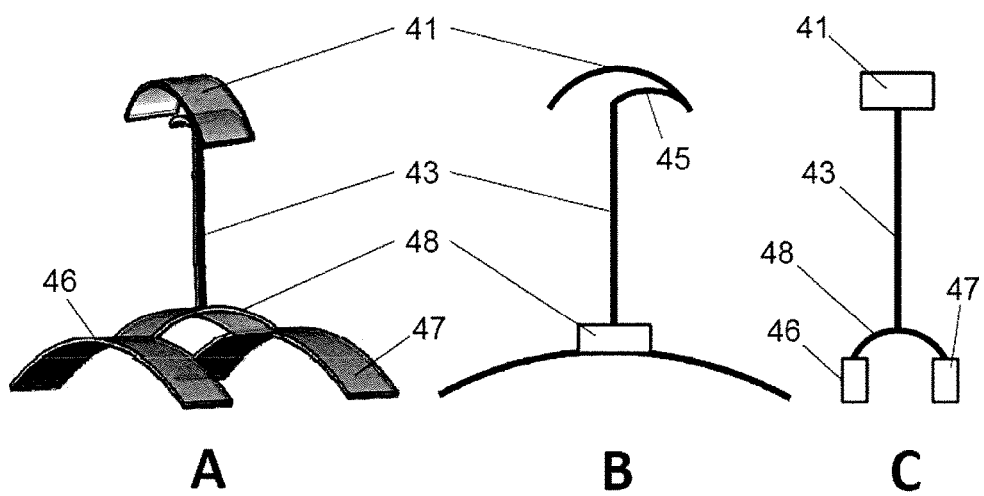
FIGS. 14A, 14B and 14C show in detail the structure of an isolated haptic or fastener in an alternative embodiment.

An alternative design of the haptic presented above and which produces a similar effect is shown in FIGS. 14A, 14B, and 14C. FIG. 14A shows a perspective view of the haptic, while FIGS. 14B and 14C show in a manner analogous to how it was shown in FIGS. 13B and 13C, the plan view and a lateral view of it, respectively. The haptic of FIGS. 14A, 14B and 14C is particularly advantageous when employing air or another gas as the central material 18 of the triplet. The most notable feature of this haptic is that the shape is formed by two independent arches 46, 47, which put pressure on the zones of the triplet shaped by the first material 17 and last material 19. Both bases 46, 47 are joined in turn by a bridge 48. In a similar manner to what occurs in the design shown in FIGS. 13A, 13B and 13C, the bases 46, 47 and the bridge 48 that joins them are completely embedded in the substrate 3. The preferred implementation of these haptics in the intraocular lens 116 is carried out by their immersion in the substrate 3 during the injection process of the silicone or the material employed for their manufacturing.

Figure 15:
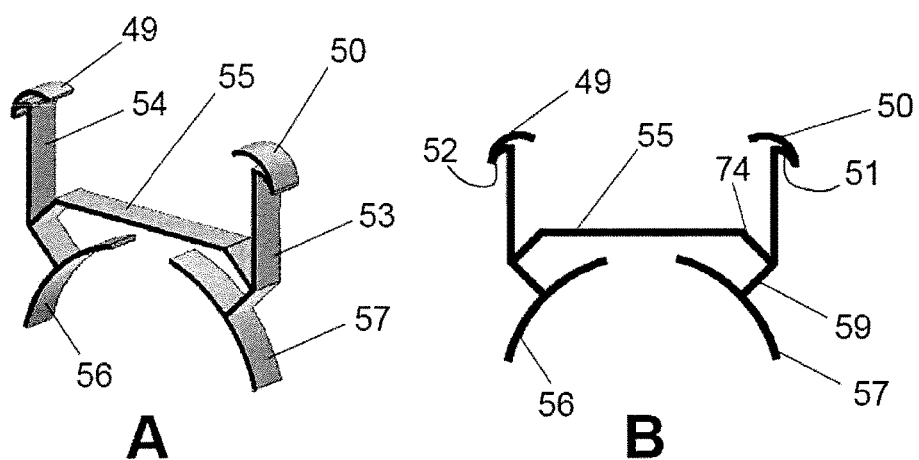
FIGS. 15A and 15B show in detail the structure of an isolated haptic or fastener in an alternative embodiment. This type is fastener is called double headed.
Figure 16:
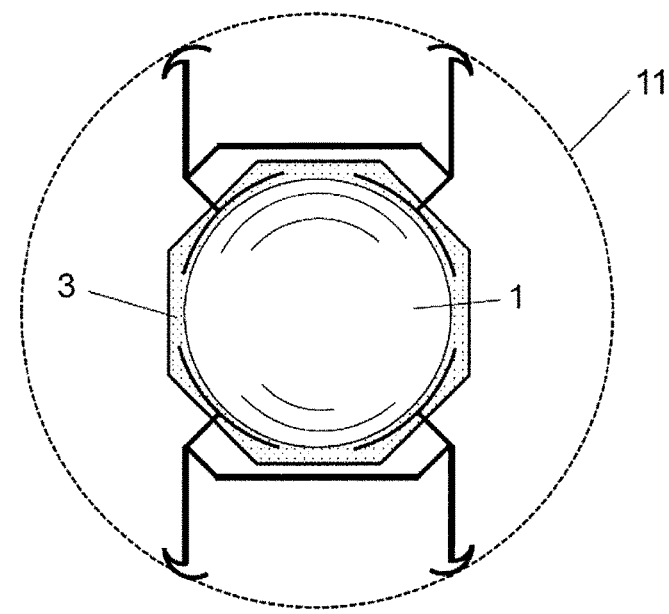
FIG. 16 shows a front view of an alternative embodiment of a variable power intraocular lens, subject of this invention, which employs a pair of so called double headed haptics.

The previously proposed haptic designs are arranged radially on the intraocular lens 116. This takes optimum advantage of the centripetal and centrifugal forces that are generated in the core of the capsule 106, the zonule 107, and, in any case, initiated by the ciliary muscle. An alternative to this arrangement of the haptics, which produces a similar effect, is shown in FIGS. 15A and 15B. In this variant the trunks of the haptics 43 do not occupy radial directions, but rather are arranged in parallel with each other. This fact may provide an advantage when folding the intraocular lens 116 in an injector for its surgical implantation through an incision in the cornea. Ideally this incision should be as small as possible for optimal healing of the cornea and to minimise the effect on its biomechanical properties. FIG. 15A shows a perspective view of the fastening system with parallel haptics, while FIG. 15B shows a front view of it. This system may be called parallel haptics or double headed. Its most significant feature is a structure on which there are two points of contact with the lens capsule 106 (49, 50), or grips to the capsular tension ring that remain joined in the design. These heads 49, 50, are provided with bridges 51, 52, which joins them to separate trunks 53, 54. Its effect is similar to what was shown in the preferred description of the haptics given above in this document. They enable, like the bridge of the simple haptic 45 shown in FIGS. 15A and 15B, providing the haptic with certain flexibility when absorbing the tensions that ultimately deform the optical zone 1 of the intraocular lens 116. The trunks 53, 54, remain joined in the structure thanks to another bridge 55. The base of this design also shows a double structure 56, 57. These bases fulfil the task of transmitting the tension to the optical zone 1 of the lens 116, to produce the change of its equatorial diameter 2. These may be carried out with a continuous structure that applies pressure on the three materials 17, 18, 19, or zones that comprise the optical zone 1, as has been described in relation to FIGS. 15A and 15B. Another alternative that produces a similar effect is to employ the double structure described in FIGS. 14A, 14B, and 14C, which is especially advisable when the central material 18 of the triplets is a gas. The two trunks 53, 54, that join the heads 49, 50, and the bases 56, 57, are coupled by the bridge 55. This forms a right angle in the zone of contact with each trunk 53, 54. The coupling zone 58, 59 of the bridge 55 with the base and the trunk 53, 54, has this particular right angle design in order to absorb the non-radial tension component that is generated when applying compression or expansion forces on the haptic structure. In this way the final force is obtained, which in the optical zone is experienced as radial. This type of haptic is incorporated into the intraocular lens 116 in pairs, as shown in FIG. 16.

Accommodative Intraocular Lens with Anchors in the Capsular Ring

The haptics previously described in this document may be implanted so that they have direct contract with the internal walls of the lens capsule 106 of the patient. In this way the tension of the lens capsule 106 directly controls the diameter of the optical zone 1 of the intraocular lens 116 and, therefore, its power. The preferred embodiment of the invention uses the capsular tension ring 42, also called the endocapsular or capsular ring, for a more efficient anchoring of the heads of the haptics 41. In this way it is possible to control with greater precision the tension that ultimately is transmitted to the optical zone 1 of the intraocular lens 116. The capsule tension rings 42 are normal elements in the surgical practice of cataract surgery. Their use is fundamental when a deficit or instability of the capsule-zonular system is noted. They are put in place as a solution to a damaged zonule 107 that is no longer capable of uniformly holding the lens capsule 106. With these rings 42, anatomically restoring the shape of the capsule 106 is attained, so that it can house an intraocular lens with guarantees after the process of extracting the natural crystalline lens 105. The alterations of the zonule 107 may result in dislocations and shifting of the intraocular lens 116, and may also produce an uneven capsular contraction. The contractions of the lens capsule 106 are ultimately responsible for the change of power in the variable power intraocular lens 116, and therefore, they must be uniform and always produced as a consequence of changes in the ciliary muscle. The implantation of the intracapsular rings also brings advantages in eyes that do not show weakness in the zonule 107, such as reducing the opacification of the posterior face of the lens capsule 106. Another very useful advantage of the variable power intraocular lenses 116 described in this invention, is their effectiveness for maintaining the circular outline of the capsular sack after the implantation of the lens 116.

Figure 17:
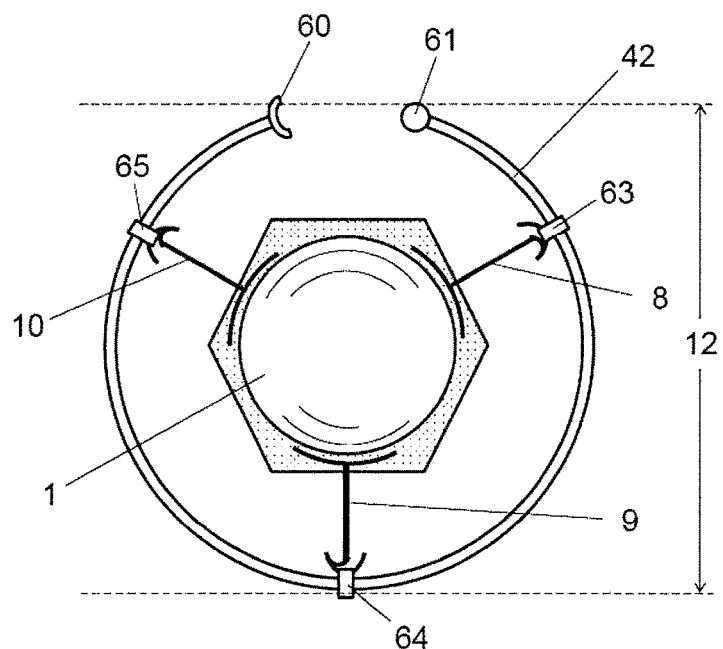
FIG. 17 shows schematically the preferred practical implementation of the intraocular lens subject of this invention, anchored on an capsular tension ring. The figure shows the situation in which the lens is unaccommodated or with less refractive power, corresponding to the maximum equatorial diameter of the intracapsular ring.
Figure 18:
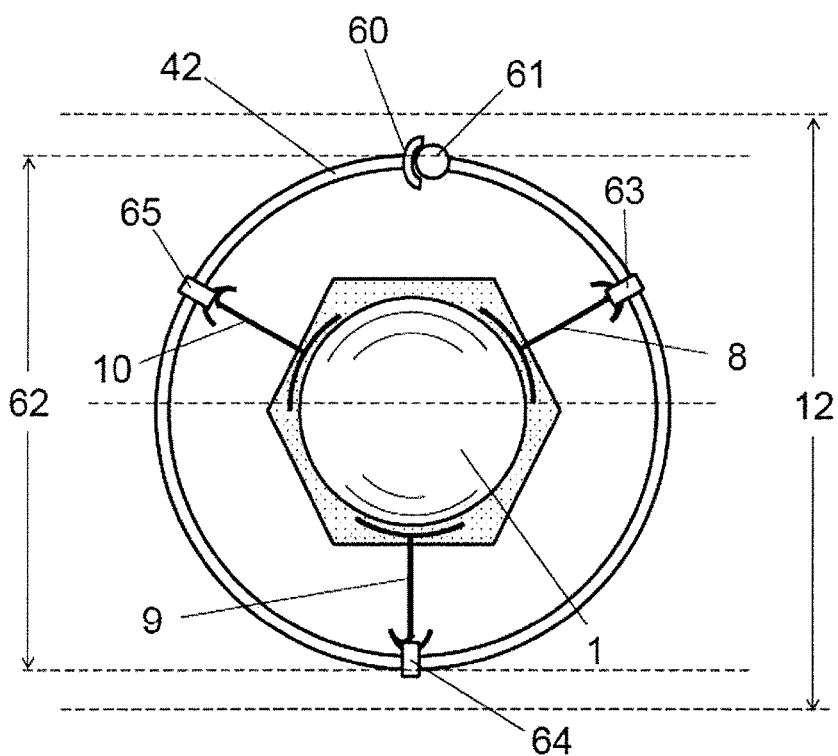
FIG. 18 shows schematically the preferred practical implementation of the intraocular lens subject of this invention, anchored on an capsular tension ring, when its diameter shows a minimum diameter. In this situation the power of the intraocular lens is maximum, corresponding to near vision.
Figure 19:
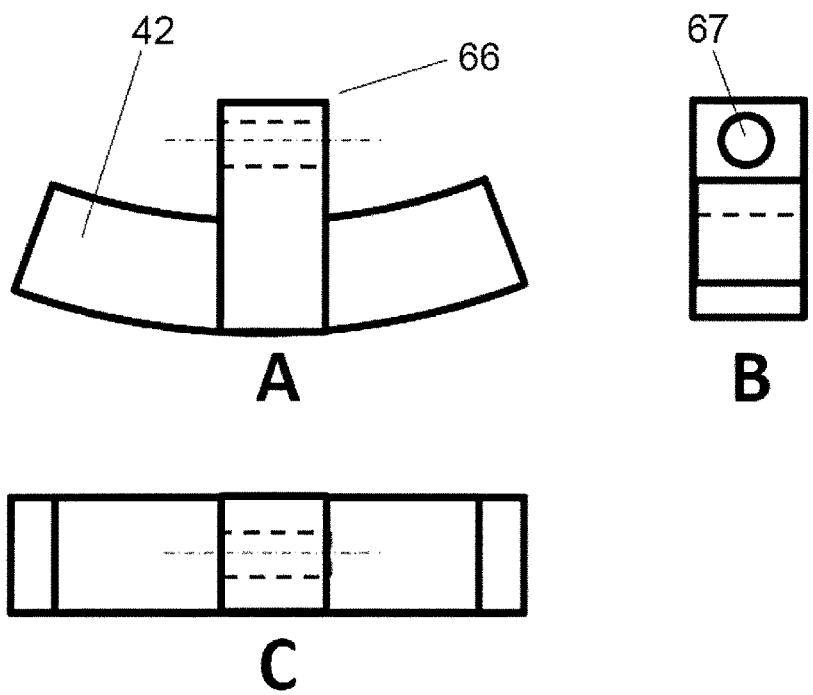
FIGS. 19A, 19B and 19C show in detail the structure of one of the anchor points for the head of the haptic, which is found on the capsular tension ring.
Figure 20:
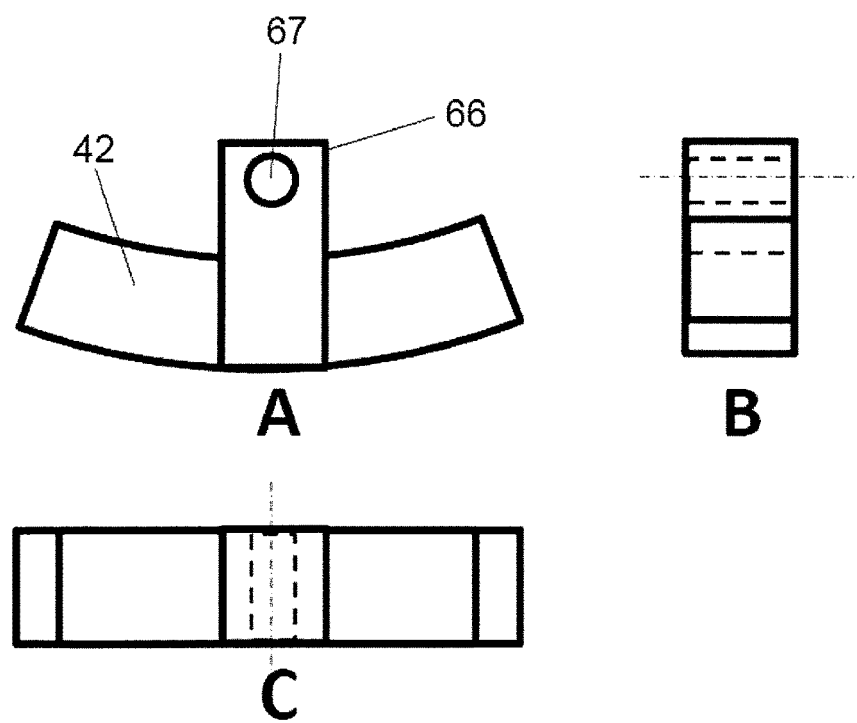
FIGS. 20A, 20B and 20C show in detail the structure of one of the anchor points for the head of the haptic, in an alternative design called frontal, which is found on the capsular tension ring.
Figure 21:
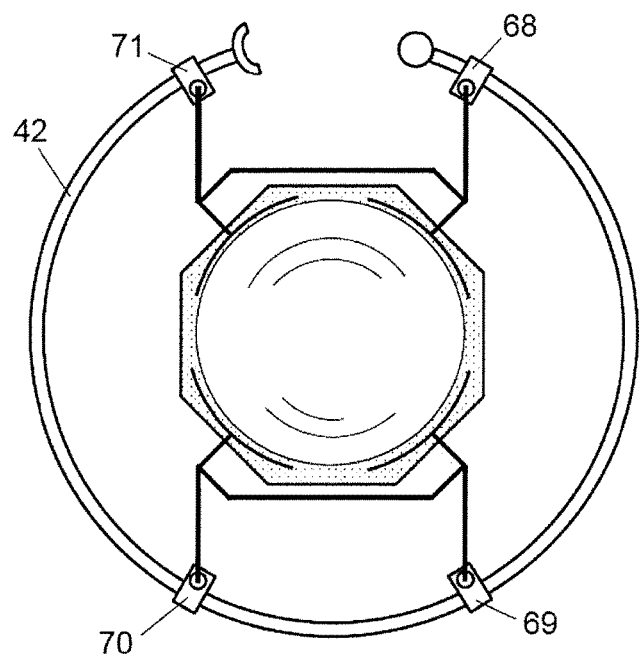
FIG. 21 shows a front view of an alternative practical embodiment of the implementation of the intraocular lens, subject of this invention, in which an intraocular lens is employed with a hexagonal substrate, having a pair of double headed haptics on a capsular tension ring provided with four front type anchors.
Figure 22:
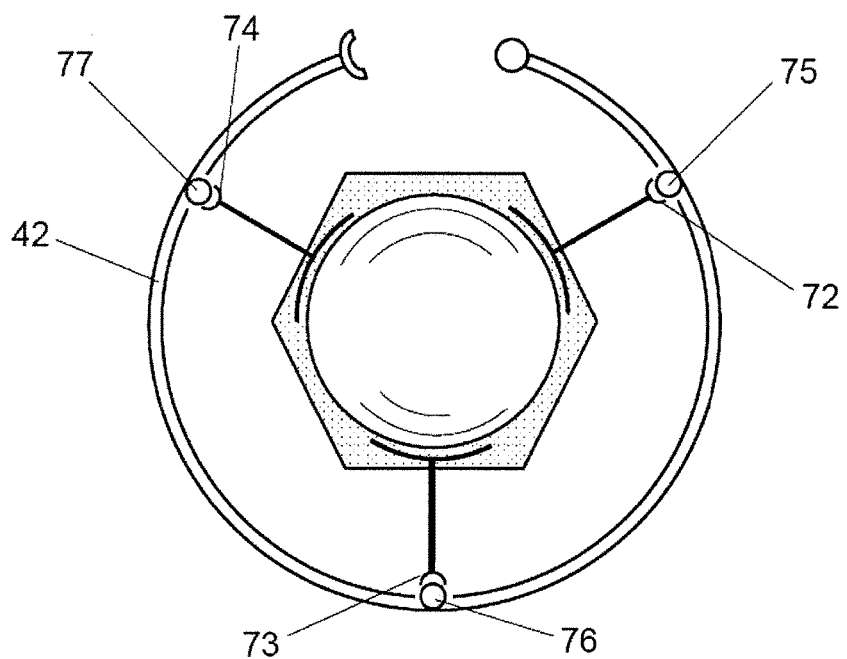
FIG. 22 shows a front view of an embodiment, as regards the practical implementation of the intraocular lens and its anchoring on the capsular tension ring. For this an intraocular lens with hexagonal substrate and three haptics are employed. Both the haptics and the anchoring of the capsular ring are provided with heads and magnetised terminations, and are held together by magnetic forces.

FIG. 17 shows a preferred embodiment of the use of the variable potential intraocular lens 116 anchored to an intracapsular tension ring 42. The capsular ring 42 is provided with some stops or terminations 60, 61, and has a free section of its circumference between them. In this way, it is possible to change the diameter 12 of ring 42 as a consequence of the changes of tension in the lens capsule 106. In its minimum diameter position 62, the stops or terminations 60, 61 couple together, as FIG. 18 shows. The shape of the terminations is concave 60 and convex 61, both being of the same diameter for a perfect coupling between them at the minimum diameter position 62 of the ring 42. Other male/female geometries for the terminations 60, 61 of the ring are possible for producing the same effect. In a preferred embodiment the intracapsular ring 42 is provided three anchor points 63, 64, 65. These are arranged on the vertices of an equilateral triangle centred in the optical zone 1 of the intraocular lens 116. The anchor points 63, 64, 65 of the ring 42 are the elements designed for housing the heads of the haptics 1. For other alternative designs of the intraocular lens 116 that produce the same accommodative effect, the arrangement of the anchor points will differ from the previously shown preferred embodiment. For example, for intraocular lenses 116 of four or six haptics, as shown in FIGS. 12A and 12B, the anchor points will be arranged naturally at regular intervals on the intracapsular ring 42. In the minimum diameter position 52 for the capsular tension ring 42, due to the stiffness of the haptics, the optical zone 1 is also in its minimum diameter 31, and therefore shows the maximum refractive power. The anchor points 62, 64, 65 essentially consist in some protuberances 66 on the intracapsular ring 42 provided with an orifice 67 that completely communicates the piece from part to part, and is where the head of the haptic 41 is inserted. For this, the surgeon must first implant the intracapsular ring 42 in order to then insert the intraocular lens 116 and begin sequentially attaching the heads of the haptics 8, 9, 10 to their housing 66. A detail of the housing or anchor of the haptic is shown in FIGS. 19A, 19B and 19C. Said figures show the three views of the housing, including a portion of the ring 42. A possible alternative embodiment that produces the same effect for the anchors is one in which the orifices for inserting the heads of the haptics 8, 9, 10 are arranged in a normal or perpendicular manner to the plane that contains the intracapsular ring 42. An example of this type of anchor is shown in FIGS. 20A, 20B and 20C. In an analogous manner, as is shown in FIGS. 19A, 19B and 19C, FIGS. 20A, 20B and 20C show the front view of the three anchor views. For the purpose of illustrating these anchors, FIG. 21 shows an alternative embodiment of the invention that employs an intraocular lens 116 with double headed haptics 49, 50, with the result that the contact zones of the ring are not equidistant, but rather, occupy the vertices of a rectangle. To be able to apply the housing 68, 69, 70, 71 with the normal orifice on the plane of ring 42, which may be called front view anchors, it is necessary for the heads of the haptic to be rotated 90 degrees with respect to those shown in the preferred embodiment in FIGS. 17 and 18. This alternative provides the potential advantage of enabling the surgeon to see the orifice 67 during the anchoring step of the heads of the haptic. A possible alternative to the preferred embodiment of the invention, and which produces the same fastening effect of the structure of the intraocular lens 116 to the intracapsular ring 42, is one that makes use of magnetic forces. For this, the head of the haptic is made from a biocompatible material with magnetic properties 72, 73, 74. In the example in FIG. 22, the magnetic heads of the haptics have a concave profile, although other geometric shapes with a similar effect are possible. The housings are made up of small spheres 75, 75, 77 having the same radius of the heads of the haptics. These are embedded in the intracapsular ring 42.

The set comprising the capsular ring 42 and the intraocular lens 116 provided with haptics 8, 9, 10 coupled to the housings 63, 64, 65, have the purpose of reliably simulating the biomechanics of the natural accommodation. For this, the capsular ring 42, when isolated, has a bigger diameter than that of the relaxed lens capsule 106, which is going to hold it. Once implanted, this ring 42 exercises a centrifugal force that stretches the lens capsule equatorially, reducing the tension of the zonule 107. The intraocular lens to be implanted has, when isolated, the maximum power for what it has been designed, and therefore, a minimum equatorial diameter of its optical zone 31. This power corresponds to the maximum accommodation that the eye is going to be provided for near vision. In an isolated situation the external diameter of the haptics 11 is less than the diameter of the capsular ring 42 implanted in the lens capsule 106. During the process of anchoring the heads of the haptics 14 in the housings 63, 64, 65, an increase of the diameter 30 in the optical zone 1 of the intraocular lens 116 is produced. The process creates an centripetal force originating in the intraocular lens 116, which tends to re-establish its rest situation with a lower diameter 31 and maximum power. This centripetal force is compensated by the centrifugal force, or expansion that the ring 42 applies against the equatorial walls of the lens capsule 106. In this situation the lens capsule 106 recovers its original size and the zonule 107 recovers its physiological tension. In this state of equilibrium, in which the compression forces of the intraocular lens 116 and the expansion forces of the ring 42 are balanced, and the power of the intraocular lens 116 reaches the necessary value to make the eye emmetropic. When the ciliary muscle contracts, the zonule 107 relaxes its tension and the lens capsule 106 applies a compression force on the set comprised by the capsular ring 42 and the intraocular lens 116, which are in an equilibrium, and therefore it does not apply any net pressure. This pressure of the lens capsule 106 is what moves the intraocular lens 116 to its rest state, with a minimum equatorial diameter 31 and, therefore, increases its power with respect of the stretched situation. This power increase, in at all events controlled at its minimum value by the diameter of the capsular ring 62, enables accommodative the view to nearby objects.

The Materials

Currently there is an enormous variety of materials that can be employed in the construction of an intraocular lens 116, both its optical portion 1 and the haptics 8, 9, 10, and, if applicable, the capsular ring 42, which are necessary for fastening it inside the lens capsule 106. Nowadays the state of the art provides a large richness of alternatives within the polymer family. Polymers are comprised of molecular chains, the fundamental unit of which is repeated to constitute the structure of the material. The properties of the basic molecule, as well as the manner of linking itself to the adjacent companions in a chain determines the overall properties of the polymer material, such as its index of refraction, water content, mechanical properties, etc. Due to the nature of the invention disclosed herein, conceived for use in the eye of a patient, it is necessary to employ a biocompatible polymer that has an absolutely inert behaviour after being implanted.

A first division of polymers can be made based on the stiffness of the material. The most significant representative of the stiff materials in the field of construction of intraocular lenses is PMMA, also known as polymethylmethacrylate. Historically it has had an important role and in fact was the first material employed for the construction of intraocular lenses. Due to its stiffness, the corneal incision required for its implantation is big compared to the one made when using other flexible polymers. The invention disclosed in this invention in relation to its optical portion 1, could be made from PMMA, although it is not described here as the most efficient option. However, this material has some very interesting properties for its incorporation in the haptics 8, 9, 10 of the intraocular lens 116, and in the capsular tension ring 42.

The preferred embodiment of this invention employs one or several flexible polymers for both its optical portion 1, and for the substrate 3. Among the existing flexible polymers there are two well differentiated groups, namely, the acrylics and silicones. In the former a useful distinction may further be made between hydrophobic and hydrophilic acrylics on the basis of their relative composition in percentage of water.

Due to the character of the invention, where the optical portion 1 is comprised by a triplet, it is possible to combine various types of polymers with similar results, maintaining the advantages of the variable power intraocular lens 116. Thus, in the field of the present invention, for designs that include three different materials for the optical portion, the use of any combination of polymers that provide similar deformation and flexibility capacity in each of the parts or refracting interfaces of the triplet is admissible. The technology allows manipulating the indexes of refraction and the mechanical properties of the polymers to obtain similar values, starting with silicones and acrylic materials, for which the preferred embodiment of this invention, as regards materials, does not need a detailed determination of the type of material used for its execution. Different alternatives give the same effect.

For designs that employ materials with a low index of refraction, such as the ones shown in FIGS. 7A, 8A and 8B, silicon is the material to be used for a preferred embodiment of the invention. For other designs that need high indexes of refraction, around 1.5, an acrylic is the material of choice.

An alternative to the use of the normal polymers, as regards the materials that comprise the triplet of the optical zone of the intraocular lens 116, is the use of photopolymerizable materials. These provide the possibility of being able to adjust their index of refraction, and even the geometric shape, through controlled ultraviolet light irradiation. The big advantage is that this operation of polymerisation may be carried out after the implantation in the eye of the patient. In this way, the success rate of the final refraction obtained is very high. The use of this type of photopolymerizable material may also be made with any of the three materials of the triplet, or in several of them simultaneously. To do this, it would be necessary to first photopolymerize the material closest to the anterior pole of the eye, and then progressively continue actuating on the posterior materials. In any event, for a correct embodiment of this modality, it is necessary to incorporate an ultraviolet light filter that prevents the radiation employed in the photopolymerization from reaching the retina of the subject.

The ultraviolet filter can be incorporated into any of the refracting interfaces comprising the intraocular lens 116, and its use does not need to be linked to the use of photopolymerizable materials. In fact, its use is beneficial for the patient in every case, inasmuch it protects the cells of the retina from this portion of the spectrum associated with pathological degenerations of various types.

For both the haptics 8, 9, 10 and the capsular tension ring 42 there are numerous alternatives that produce a similar effect as regards the properties and advantages of the present invention. Thus, PMMA, polypropylene, polyamide and polyvinylidene fluoride, PVDF or a combination thereof, may be used for the embodiment of the alternatives. All of the aforesaid materials are routinely used in the manufacture of haptics in the field of intraocular lens.

A detailed description of the invention has been drawn up, with its preferred embodiments and also alternatives in many cases. However, there are other relatively obvious modifications or variants to a person skilled in the field of intraocular lens design that have not been explicitly included. These other possible embodiments, which are based on the same principles and ideas disclosed in the present invention, must also be understood as covered and protected by the present document.

The following numerical references are linked to the different elements described and represented in the present document:

1. Optical zone of the intraocular lens
2. Diameter of the optical zone of the intraocular lens.
3. Support or fastening substrate for the optical zone of the intraocular lens.
4. Exterior diameter that completely contains substrate 3.
5. Optical zone and substrate of the intraocular lens having a circular geometry.
6. Optical zone and substrate of the intraocular having a regular decagon shape.
7. Optical zone and substrate of the intraocular lens having a regular dodecagon shape.
8. Haptic or simple headed haptic, together with 9 and 10 of the intraocular lens.
9. Haptic or simple headed haptic, together with 8 and 10 of the intraocular lens.
10. Haptic or simple headed haptic, together with 8 and 9 of the intraocular lens.
11. Virtual circumference that encircles the haptics of the intraocular lens.
12. Diameter of the virtual circumference that encircles the haptics in its stretched or far vision state.
13. First refracting surface of the triplet that forms the optical zone of the intraocular lens, separating the aqueous humour and the first material of the lens
14. Second refracting surface of the triplet that forms the optical zone of the intraocular lens, separating the first and second first material of the lens
15. Third refracting surface of the triplet that forms the optical zone of the intraocular lens, separating the second and third material of the lens
16. Fourth refracting surface of the triplet that forms the optical zone of the intraocular lens, separating the third material of the lens of the aqueous humour.
17. First material of the triplet that forms the optical zone of the intraocular lens.
18. Second material of the triplet that forms the optical zone of the intraocular lens.
19. Third material of the triplet that forms the optical zone of the intraocular lens.
20. Haptic or fastener of an alternative embodiment of the intraocular lens comprised of the same material as the substrate, together with 21 and 22.
21. Haptic or fastener of an alternative embodiment of the intraocular lens comprised of the same material as the substrate, together with 20 and 22.
22. Haptic or fastener of an alternative embodiment of the intraocular lens comprised of the same material as the substrate, together with 20 and 21.
23. Curvature radius of the first refracting surface of the triplet that forms the optical zone of the intraocular lens, in its stretched or far vision state.
24. Curvature radius of the second refracting surface of the triplet that forms the optical zone of the intraocular lens, in its stretched or far vision state.
25. Curvature radius of the third refracting surface of the triplet that forms the optical zone of the intraocular lens, in its stretched or far vision state.
26. Curvature radius of the fourth refracting surface of the triplet that forms the optical zone of the intraocular lens, in its stretched or far vision state.
27. Thickness of the first material of the triplet that forms the optical zone of the intraocular lens, in its stretched or far vision state.

28. Thickness of the second material of the triplet that forms the optical zone of the intraocular lens, in its stretched or far vision state.
29. Thickness of the third material of the triplet that forms the optical zone of the intraocular lens, in its stretched or far vision state.
0 30. Equatorial diameter of the optical zone of the intraocular lens, in its stretched or far vision state.
31. Equatorial diameter of the optical zone of the intraocular lens, in its compressed or near vision state.
32. Curvature radius of the first refracting surface of the triplet that forms the optical zone of the intraocular lens, in its compressed or near vision state.
33. Curvature radius of the second refracting surface of the triplet that forms the optical zone of the intraocular lens, in its compressed or near vision state.
34. Curvature radius of the third refracting surface of the triplet that forms the optical zone of the intraocular lens, in its compressed or near vision state.
35. Curvature radius of the fourth refracting surface of the triplet that forms the optical zone of the intraocular lens, in its compressed or near vision state.
36. Thickness of the first material of the triplet that forms the optical zone of the intraocular lens, in its compressed or near vision state.
37. Thickness of the second material of the triplet that forms the optical zone of the intraocular lens, in its compressed or near vision state.
38. Thickness of the third material of the triplet that forms the optical zone of the intraocular lens, in its compressed or near vision state.
39. Optical axis of the intraocular lens
40. Axis of symmetry contained in the sagittal plane of the optical zone of the intraocular lens.
41. Simple head of the haptic or fastener.
42. Capsular tension ring.
43. Trunk of the haptic or fastener.
44. Base or simple arc of the haptic or fastener.
45. Joining bridge between the head and trunk of the haptic or fastener.
46. One of the arcs, together with 47, that forms the base of the haptic in its double base version.
47. One of the arcs, together with 46, that forms the base of the haptic in its double base version.
48. Joining bridge between the two arcs that form the base of the haptic in its double base version.
49. One of the heads, together with 50, that form the haptic or fastener called parallel or double headed haptics.
50. One of the heads, together with 49, that form the haptic or fastener called parallel or double headed haptics.
51. Joining bridge, together with 52, between one of the heads and one of the trunks of the haptic or fastener called parallel or double headed haptics.
52. Joining bridge, together with 51, between one of the heads and one of the trunks of the haptic or fastener called parallel or double headed haptics.
53. One of the trunks, together with 54, of the haptic or fastener called parallel or double headed haptics.
54. One of the trunks, together with 53, of the haptic or fastener called parallel or double headed haptics.
55. Joining bridge between the two trunks of the haptic or fastener called parallel or double headed haptics.
56. One of the arcs, together with 57, that form the base of the haptic or fastener called parallel or double headed haptics.
57. One of the arcs, together with 56, that form the base of the haptic or fastener called parallel or double headed haptics.
58. Coupling segment, together with 59, of the joining bridge between the two trunks with one of them on the haptic or fastener called parallel or double headed haptics.
59. Coupling segment, together with 58, of the joining bridge between the two trunks with one of them on the haptic or fastener called parallel or double headed haptics.
60. One of the terminations, together with 61, with a concave shape of the capsular tension ring.
61. One of the terminations, together with 60, with a convex shape of the capsular tension ring.
62. Diameter of the virtual circumference that encircles the haptics, in its compressed or near vision state.
63. One of the anchors, together with 64 and 65, of the capsular tension ring that houses the head of the haptic or fastener of the intraocular lens.
64. One of the anchors, together with 63 and 65, of the capsular tension ring that houses the head of the haptic or fastener of the intraocular lens.
65. One of the anchors, together with 63 and 64, of the capsular tension ring that houses the head of the haptic or fastener of the intraocular lens.
66. Internal protuberance of the capsular tension ring that supports the head of the haptic or fastener of the intraocular lens.
67. Orifice that traverses the protuberance of the capsular tension ring and serves for housing the head of the haptic or fastener of the intraocular lens.
68. Front view of one of the anchors, together with 69, 70, and 71, arranged in the capsular tension ring, the orifices of which for inserting the heads of the haptics are arranged in a normal manner to the plane that contains the intracapsular ring.
69. Front view of one of the anchors, together with 68, 70, and 71, arranged in the capsular tension ring, the orifices of which for inserting the heads of the haptics are arranged in a normal manner to the plane that contains the intracapsular ring.
70. Front view of one of the anchors, together with 68, 69, and 71, arranged in the capsular tension ring, the orifices of which for inserting the heads of the haptics are arranged in a normal manner to the plane that contains the intracapsular ring.
71. Front view of one of the anchors, together with 68, 69, and 70, arranged in the capsular tension ring, the orifices of which for inserting the heads of the haptics are arranged in a normal manner to the plane that contains the intracapsular ring.
72. Head of the haptic of the intraocular lens, together with 73 and 74, in a concave shape that is coupled to the ring by magnetic forces.
73. Head of the haptic of the intraocular lens, together with 72 and 74, in a concave shape that is coupled to the ring by magnetic forces.
74. Head of the haptic of the intraocular lens, together with 72 and 73, in a concave shape that is coupled to the ring by magnetic forces.
75. Convex protuberance, together with 76 and 77, on the internal face of the capsular tension that couples a haptic with a concave shaped head of the intraocular lens by magnetic forces.
76. Convex protuberance, together with 75 and 77, on the internal face of the capsular tension that couples a haptic with a concave shaped head of the intraocular lens by magnetic forces.

77. Convex protuberance, together with 75 and 76, on the internal face of the capsular tension that couples a haptic with a concave shaped head of the intraocular lens by magnetic forces.
101. Cornea.
102. Anterior chamber.
103. Iris.
103.bis. Pupil
104. Posterior chamber.
105. Unaccommodated crystalline lens.
105bis. Accommodated crystalline lens.
106. Stretched or unaccommodated lens capsule
106bis. Contracted or accommodated lens capsule
107. Zonule.
108. Ciliary muscle in relaxed state.
108bis Ciliary muscle in contracted state.
109. Sclera.
110. Ciliary sulcus.
111. Vitreous humour.
112. Retina.
113. Optical axis.
114. Fovea
115. Visual axis.
116. Intraocular lens.

The invention claimed is:

1. A variable power accommodative intraocular lens, comprising:
an optical zone (1),
a substrate (3) that surrounds said optical zone (1), wherein the substrate holds the optical zone and transmits external forces to the optical zone, and
a plurality of mechanical haptics (8, 9, 10), wherein each of the plurality of mechanical haptics comprises a base that is disposed on the substrate (3) and that transmits the external forces to said substrate (3),
wherein the optical zone (1) comprises a plurality of materials having a single common optical axis, the plurality of materials comprising a first material, a second material, and a central material each of which has the same equatorial diameter, the first and the second materials sandwiching the central material, the first and the second materials having respective indices of refraction that are different from an index of refraction of the central material,
wherein the plurality of materials, when implanted in an eye of a subject, provide the variable power accommodative intraocular lens with at least four refracting interfaces (13, 14, 15, 16),
wherein each of the plurality of materials has an equatorial end and the respective equatorial ends of the plurality of materials are joined by said substrate (3),
wherein each of the plurality of materials is flexible and deformable in response to the external forces, and wherein the plurality of mechanical haptics, the substrate and the plurality of materials are configured with respect to one another such that, with the intraocular lens implanted in the eye of the subject and operatively engaged with ciliary muscles of the eye, a force applied by the ciliary muscles is transmitted by the plurality of mechanical haptics to the substrate to effect a compression or stretching of the equatorial diameter of the optical zone that changes a refractive power of the variable power accommodative intraocular lens.

2. The variable power accommodative intraocular lens according to claim 1, wherein the central material (18) of the optical zone (1) does not comprise a fluid, a gas, or air.

3. The variable power accommodative intraocular lens according to claim 1, wherein at least one of the refracting interfaces (13, 14, 15, 16) of the optical zone (1) has an apodization in amplitude or an aspheric surface.

4. The variable power accommodative intraocular lens according to claim 1, wherein the plurality of haptics (8, 9, 10) are arranged in a radial manner with respect to the optical zone (1) such that the external forces transmitted by the mechanical haptics to the substrate are centripetal or centrifugal forces, wherein at least one of the plurality of bases is embedded in the substrate (3), and wherein each of the plurality of haptics comprises at least one trunk (43), and at least one head (41).

5. The variable power accommodative intraocular lens according to claim 4, wherein the head (41) has a shape of a half moon and is joined with the trunk (43) by an element with another half moon shape.

6. The variable power accommodative intraocular lens according to claim 4, wherein the plurality of bases comprise first and second bases in the shape of arcs (46, 47), joined by a bridge (48), the first and second bases (46, 47) and the bridge (48) being completely embedded in the substrate (3).

7. The variable power accommodative intraocular lens according to claim 1, wherein first and second of the plurality of haptics (8, 9, 10) are disposed parallel to each other and each of the first and second haptics comprises at least one base (44) embedded in the substrate (3), at least one trunk (43), and at least one head (41).

8. The variable power accommodative intraocular lens according to claim 7, wherein each of the first and second haptics comprises a plurality of heads (49, 50), a plurality of haptic bridges, a plurality of trunks, a plurality of haptic bases, a plurality of couplers and a connecting bridge (55), wherein the haptic bridges (51, 52) join the plurality of heads to respective of the plurality of trunks (53, 54), the connecting bridge connects first and second of the plurality of trunks (53, 54), and the plurality of couplers join the connecting bridge (55) to the plurality of haptic bases (56, 57).

9. The variable power accommodative intraocular lens according to claim 1, wherein each of the first material, the second material and the central material comprises a photopolymerizable material.

10. The variable power accommodative intraocular lens according to claim 1, wherein each of the first, the second and the central materials is different from each other.

11. The variable power accommodative intraocular lens according to claim 1, wherein the first material and the second material are the same.

12. The variable power accommodative intraocular lens according to claim 1, wherein the first, the second and the central materials are selected such that a contraction of the equatorial diameter of the optical zone of 14 µm or less results in a redistribution of respective thicknesses of the first, the second and the central materials that produces a change in respective radii of curvature of the at least four refracting interfaces and causes an increase in power of the variable power accommodative intraocular lens of at least 4 dioptres.

13. The variable power accommodative intraocular lens according to claim 1, wherein the first, the second and the central materials are selected such that a contraction of the equatorial diameter of the optical zone of 4 µm results in a redistribution of respective thicknesses of the first, the second and the central materials that produces a change in respective radii of curvature of the at least four refracting interfaces and causes an increase in power of the variable power accommodative intraocular lens of at least 4 dioptres.

14. The variable power accommodative intraocular lens according to claim 1, wherein the lens is stretchable from a non-stretched configuration to a stretched configuration and wherein each of the first and the second materials has a central portion with a thickness that is as large or larger than a thickness at peripheral portions of the first and the second materials with the lens in the stretched configuration.

* * * * *